United States Patent
Biemans et al.

(10) Patent No.: US 10,245,317 B2
(45) Date of Patent: *Apr. 2, 2019

(54) IMMUNOGENIC COMPOSITION

(71) Applicant: GlaxoSmithKline Biologicals s.a., Rixensart (BE)

(72) Inventors: Ralph Leon Biemans, Rixensart (BE); Dominique Boutriau, Rixensart (BE); Carine Capiau, Rixensart (BE); Philippe Denoel, Rixensart (BE); Pierre Duvivier, Rixensart (BE); Jan Poolman, Rixensart (BE)

(73) Assignee: GLAXOSMITHKLINE BIOLOGICALS S.A., Rixensart (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/265,597

(22) Filed: Sep. 14, 2016

(65) Prior Publication Data

US 2017/0065714 A1    Mar. 9, 2017

Related U.S. Application Data

(63) Continuation of application No. 11/917,702, filed as application No. PCT/EP2006/006269 on Jun. 23, 2006, now Pat. No. 9,486,515.

(30) Foreign Application Priority Data

| Jun. 27, 2005 | (GB) | .................................. | 0513069.5 |
| Jun. 27, 2005 | (GB) | .................................. | 0513071.1 |
| Jul. 28, 2005 | (GB) | .................................. | 0515556.9 |
| Nov. 28, 2005 | (GB) | .................................. | 0524204.5 |
| Dec. 21, 2005 | (GB) | .................................. | 0526040.1 |
| Dec. 21, 2005 | (GB) | .................................. | 0526041.9 |

(51) Int. Cl.

| *A61K 39/00* | (2006.01) |
| *A61K 39/02* | (2006.01) |
| *C07H 3/00* | (2006.01) |
| *C12N 7/00* | (2006.01) |
| *A61K 39/08* | (2006.01) |
| *A61K 39/09* | (2006.01) |
| *A61K 39/385* | (2006.01) |
| *A61K 39/095* | (2006.01) |
| *A61K 39/102* | (2006.01) |
| *A61K 39/116* | (2006.01) |
| *A61K 39/05* | (2006.01) |
| *A61K 39/29* | (2006.01) |
| *A61K 39/145* | (2006.01) |
| *A61K 39/12* | (2006.01) |

(52) U.S. Cl.
CPC ........ *A61K 39/385* (2013.01); *A61K 39/0017* (2013.01); *A61K 39/0018* (2013.01); *A61K 39/05* (2013.01); *A61K 39/08* (2013.01); *A61K 39/092* (2013.01); *A61K 39/095* (2013.01); *A61K 39/099* (2013.01); *A61K 39/102* (2013.01); *A61K 39/116* (2013.01); *A61K 39/145* (2013.01); *A61K 39/292* (2013.01); *C07H 3/00* (2013.01); *C12N 7/00* (2013.01); *A61K 39/12* (2013.01); *A61K 2039/545* (2013.01); *A61K 2039/55* (2013.01); *A61K 2039/575* (2013.01); *A61K 2039/6037* (2013.01); *A61K 2039/62* (2013.01); *A61K 2039/627* (2013.01); *A61K 2039/70* (2013.01); *C12N 2730/10134* (2013.01); *C12N 2760/16234* (2013.01); *C12N 2760/16271* (2013.01); *C12N 2770/32634* (2013.01); *Y02A 50/466* (2018.01); *Y02A 50/472* (2018.01); *Y02A 50/484* (2018.01)

(58) Field of Classification Search
None
See application file for complete search history.

(56) References Cited

U.S. PATENT DOCUMENTS

| 4,057,685 A | 11/1977 | McIntire |
| 4,235,877 A | 11/1980 | Fullerton |
| 4,365,170 A | 12/1982 | Okuhara |
| 4,459,286 A | 7/1984 | Hilleman et al. |
| 4,673,574 A | 6/1987 | Anderson |
| 4,709,017 A | 11/1987 | Collier et al. |
| 4,727,136 A | 2/1988 | Jennings et al. |
| 4,808,700 A | 2/1989 | Anderson et al. |
| 4,950,740 A | 8/1990 | Greenfield et al. |

(Continued)

FOREIGN PATENT DOCUMENTS

| CA | 2004810 A | 6/1990 |
| CN | 1401328 A | 3/2003 |

(Continued)

OTHER PUBLICATIONS

Bartoloni et al, Immunogenicity of meningococcal B polysaccharide conjugated to tetanus toxoid or CRM197 via adipic acid dihydrazide. Vaccine, 1995, 13/5:463-470 (Year: 1995).*

(Continued)

*Primary Examiner* — Nita M. Minnifield
(74) *Attorney, Agent, or Firm* — Seed IP Law Group LLP

(57) ABSTRACT

The present application discloses an immunogenic composition comprising at least 2 different *N. meningitidis* capsular saccharides, wherein one or more is/are selected from a first group consisting of MenA, MenC, MenY and MenW which is/are conjugated through a linker to a carrier protein(s), and one or more different saccharides is/are selected from a second group consisting of MenA, MenC, MenY and MenW which is/are directly conjugated to a carrier protein(s).

11 Claims, 1 Drawing Sheet

(56) References Cited

U.S. PATENT DOCUMENTS

| | | |
|---|---|---|
| 5,651,971 A | 7/1997 | Lees |
| 5,843,711 A | 12/1998 | Collier et al. |
| 5,849,301 A | 12/1998 | Lees |
| 5,869,058 A | 2/1999 | Cohen et al. |
| 5,917,017 A | 6/1999 | Collier et al. |
| 5,965,714 A | 10/1999 | Ryall |
| 6,146,902 A | 11/2000 | McMaster |
| 6,251,401 B1 | 6/2001 | Ceccarini et al. |
| 6,455,673 B1 | 9/2002 | Collier |
| 6,855,321 B1 | 2/2005 | Rappuoli et al. |
| 7,018,637 B2 | 3/2006 | Chong et al. |
| 7,122,191 B2 | 10/2006 | Dominowski et al. |
| 7,628,995 B2 | 12/2009 | Bos et al. |
| 7,838,014 B2 | 11/2010 | Biemans et al. |
| 8,039,007 B2 | 10/2011 | Rappuoli et al. |
| 8,173,135 B2* | 5/2012 | Lee ............... A61K 39/385 424/184.1 |
| 8,221,770 B2 | 7/2012 | Biemans et al. |
| 8,259,461 B2 | 9/2012 | Hollis |
| 8,309,327 B2 | 11/2012 | Biemans et al. |
| 8,329,184 B2* | 12/2012 | Biemans ........... A61K 39/095 424/184.1 |
| 8,398,983 B2* | 3/2013 | Biemans ........... A61K 39/095 424/184.1 |
| 8,409,587 B2 | 4/2013 | Mayeresse et al. |
| 8,431,136 B2* | 4/2013 | Biemans ........... A61K 39/095 424/197.11 |
| 8,574,596 B2 | 11/2013 | Castado et al. |
| 8,679,770 B2 | 3/2014 | De Vleeschauwer et al. |
| 8,703,148 B2* | 4/2014 | Biemans ........... A61K 39/085 424/184.1 |
| 8,753,645 B2* | 6/2014 | Biemans ........... A61K 39/092 424/194.1 |
| 8,815,254 B2 | 8/2014 | Biemans et al. |
| 8,846,049 B2* | 9/2014 | Biemans ........... A61K 39/095 424/184.1 |
| 8,846,080 B2 | 9/2014 | Biemans et al. |
| 8,858,955 B2 | 10/2014 | Biemans et al. |
| 8,883,163 B2* | 11/2014 | Biemans ........... A61K 39/095 424/184.1 |
| 8,895,024 B2 | 11/2014 | Hausdorff et al. |
| 8,895,724 B2 | 11/2014 | Hausdorff et al. |
| 8,945,582 B2 | 2/2015 | De Hemptinne et al. |
| 8,956,625 B2 | 2/2015 | De Hemptinne et al. |
| 8,999,354 B2 | 4/2015 | Ryall |
| 9,044,157 B2 | 6/2015 | Adachi et al. |
| 9,107,872 B2 | 8/2015 | Biemans et al. |
| 9,168,313 B2* | 10/2015 | Capiau ............... A61K 39/092 |
| 9,175,033 B2* | 11/2015 | Lee ................... A61K 39/385 |
| 9,180,204 B2 | 11/2015 | Contorni |
| 9,198,977 B2 | 12/2015 | Kapre et al. |
| 9,233,151 B2* | 1/2016 | Boutriau ............ A61K 39/102 |
| 9,259,461 B2 | 2/2016 | Bos et al. |
| 9,265,839 B2* | 2/2016 | Biemans ............ A61K 39/092 |
| 9,265,840 B2* | 2/2016 | Biemans ............ A61K 39/092 |
| 9,358,279 B2* | 6/2016 | Biemans ............ A61K 39/095 |
| 9,365,624 B2 | 6/2016 | Poolman et al. |
| 9,486,515 B2* | 11/2016 | Biemans ............ A61K 39/095 |
| 9,493,517 B2* | 11/2016 | Costantino ........ A61K 39/095 |
| 9,694,064 B2* | 7/2017 | Boutriau ............ A61K 39/08 |
| 9,839,686 B2* | 12/2017 | Berti ................. A61K 39/385 |
| 9,884,113 B2* | 2/2018 | Biemans ............ A61K 39/092 |
| 9,931,397 B2* | 4/2018 | Biemans ............ A61K 39/095 |
| 10,130,694 B2* | 11/2018 | Boutriau et al. ..... A61K 39/092 |
| 2003/0099672 A1 | 5/2003 | Schultz |
| 2003/0180316 A1 | 9/2003 | Boutriau et al. |
| 2004/0096461 A1 | 5/2004 | Michon et al. |
| 2004/0126389 A1 | 7/2004 | Berthet et al. |
| 2004/0202668 A1 | 10/2004 | Boutriau et al. |
| 2004/0213804 A1 | 10/2004 | Michon et al. |
| 2005/0019337 A1 | 1/2005 | Ryall |
| 2005/0025780 A1 | 2/2005 | Rubido et al. |
| 2008/0193476 A1 | 8/2008 | Biemans et al. |
| 2008/0199490 A1 | 8/2008 | Biemans et al. |
| 2008/0260773 A1 | 10/2008 | Del Giudice et al. |
| 2008/0305127 A1 | 12/2008 | Poolman |
| 2009/0010959 A1 | 1/2009 | Biemans et al. |
| 2009/0017059 A1 | 1/2009 | Biemans et al. |
| 2009/0017072 A1 | 1/2009 | Biemans et al. |
| 2009/0041802 A1 | 2/2009 | Biemans et al. |
| 2009/0043077 A1 | 2/2009 | Berti |
| 2009/0060945 A1 | 3/2009 | Marshall |
| 2009/0136541 A1 | 5/2009 | Biemans et al. |
| 2009/0162394 A1 | 6/2009 | Biemans et al. |
| 2009/0214586 A1 | 8/2009 | Contorni et al. |
| 2009/0252759 A1 | 10/2009 | Biemans et al. |
| 2009/0311285 A1 | 12/2009 | Biemans et al. |
| 2010/0074918 A1 | 3/2010 | Poolman |
| 2010/0104593 A1 | 4/2010 | Marshall |
| 2010/0143399 A1 | 6/2010 | Biemans et al. |
| 2010/0183662 A1 | 7/2010 | Biemans et al. |
| 2010/0203137 A1 | 8/2010 | Contorni et al. |
| 2010/0209450 A1 | 8/2010 | Biemans et al. |
| 2010/0215686 A1 | 8/2010 | Biemans et al. |
| 2013/0171188 A1 | 7/2013 | Biemans et al. |
| 2013/0216571 A1 | 8/2013 | Ryall |
| 2015/0004191 A1 | 1/2015 | Contorni |
| 2015/0044253 A1 | 2/2015 | Biemans et al. |
| 2015/0104479 A1 | 4/2015 | Romano et al. |
| 2015/0265702 A1 | 9/2015 | Biemans et al. |
| 2016/0129101 A1* | 5/2016 | Biemans ............ A61K 39/085 424/190.1 |
| 2016/0303215 A1* | 10/2016 | Marshall ........... A61K 39/095 |
| 2016/0354457 A1* | 12/2016 | Costantino ......... C07K 14/22 |
| 2017/0043004 A1* | 2/2017 | Costantino ........ A61K 39/095 |
| 2017/0056490 A1* | 3/2017 | Biemans ............ A61K 39/085 |
| 2017/0065714 A1* | 3/2017 | Biemans ............ A61K 39/095 |
| 2017/0224803 A1* | 8/2017 | Berti ................. A61K 39/092 |
| 2018/0064806 A1* | 3/2018 | Biemans ............ A61K 39/095 |
| 2018/0104322 A1* | 4/2018 | Biemans ............ A61K 47/646 |
| 2018/0104323 A1* | 4/2018 | Denoel ............... A61K 47/646 |
| 2018/0207262 A1* | 7/2018 | Biemans ............ A61K 39/092 |
| 2018/0214532 A1* | 8/2018 | Jansen ............... A61K 47/6415 |

FOREIGN PATENT DOCUMENTS

| | | |
|---|---|---|
| CN | 1425465 A | 6/2003 |
| CN | 1709505 A | 12/2005 |
| EP | 0 211 258 A2 | 2/1987 |
| EP | 0 161 188 B1 | 4/1991 |
| EP | 0 208 375 B1 | 12/1991 |
| EP | 0 378 881 B1 | 6/1993 |
| EP | 0 594 950 A1 | 5/1994 |
| EP | 0 427 347 B1 | 2/1995 |
| EP | 0 477 508 B1 | 7/1995 |
| EP | 0 471 177 B1 | 10/1995 |
| EP | 0 497 524 B1 | 7/1998 |
| EP | 0 497 525 B1 | 8/1998 |
| EP | 0 594 610 B1 | 9/1998 |
| EP | 0 941 738 A1 | 9/1999 |
| EP | 1 946 769 B1 | 5/2012 |
| WO | 91/01146 A1 | 2/1991 |
| WO | 91/08772 A1 | 6/1991 |
| WO | 93/15760 A1 | 8/1993 |
| WO | 93/17712 A2 | 9/1993 |
| WO | 93/24148 A1 | 12/1993 |
| WO | 94/03208 A1 | 2/1994 |
| WO | 95/08348 A1 | 3/1995 |
| WO | 96/14086 A1 | 5/1996 |
| WO | 96/29094 A1 | 9/1996 |
| WO | 96/40242 A1 | 12/1996 |
| WO | 97/00697 A1 | 1/1997 |
| WO | 97/35613 A1 | 10/1997 |
| WO | 98/42721 A1 | 10/1998 |
| WO | 98/51339 A1 | 11/1998 |
| WO | 98/58668 A2 | 12/1998 |
| WO | 99/13906 A1 | 3/1999 |
| WO | 99/42130 A1 | 8/1999 |
| WO | 99/48525 A1 | 9/1999 |
| WO | 00/10599 A2 | 3/2000 |
| WO | 00/50006 A2 | 8/2000 |
| WO | 00/56360 A2 | 9/2000 |
| WO | 00/61761 A2 | 10/2000 |

(56) References Cited

FOREIGN PATENT DOCUMENTS

| | | |
|---|---|---|
| WO | 01/00790 A1 | 1/2001 |
| WO | 01/30390 A2 | 5/2001 |
| WO | 01/41800 A2 | 6/2001 |
| WO | 01/72337 A1 | 10/2001 |
| WO | 02/00249 A2 | 1/2002 |
| WO | 02/058737 A2 | 8/2002 |
| WO | 02/080965 A2 | 10/2002 |
| WO | 02/091998 A2 | 11/2002 |
| WO | 03/007985 A2 | 1/2003 |
| WO | 03/078453 A1 | 9/2003 |
| WO | 03/080678 A1 | 10/2003 |
| WO | 03/094834 A2 | 11/2003 |
| WO | 03/094960 A2 | 11/2003 |
| WO | 2004/011027 A1 | 2/2004 |
| WO | 2004/032958 A1 | 4/2004 |
| WO | 2004/048404 A2 | 6/2004 |
| WO | 2004/067030 A2 | 8/2004 |
| WO | WO-2004067030 A2 * | 8/2004 ............ C07K 14/22 |
| WO | 2004/083251 A2 | 9/2004 |
| WO | 2004/103400 A2 | 12/2004 |
| WO | 2004/110480 A2 | 12/2004 |
| WO | 2005/000345 A2 | 1/2005 |
| WO | 2005/020964 A1 | 3/2005 |
| WO | 2005/032583 A2 | 4/2005 |
| WO | 2005/089794 A2 | 9/2005 |
| WO | 2005/105140 A2 | 11/2005 |
| WO | 2006/075170 A1 | 7/2006 |
| WO | 2006/097851 A2 | 9/2006 |
| WO | 2007/000322 A1 | 1/2007 |
| WO | 2007/000327 A1 | 1/2007 |
| WO | 2007/000341 A2 | 1/2007 |
| WO | 2007/000342 A2 | 1/2007 |
| WO | 2007/000343 A2 | 1/2007 |
| WO | 2008/011201 A2 | 1/2008 |
| WO | 2008/081014 A2 | 7/2008 |
| WO | 2008/081022 A1 | 7/2008 |
| WO | 2008/135514 A1 | 11/2008 |
| WO | 2008/149238 A2 | 12/2008 |
| WO | 2009/016515 A2 | 2/2009 |
| WO | WO-2017067962 A1 * | 4/2017 ........... A61K 39/092 |

OTHER PUBLICATIONS

Cabrera et al, Immunogenicity of conjugates of Neisseria meningitidis serogroup C polysaccharide bound to tetanus toxoid by different spacer arms. Revista CENIC, Ciencias Biologicas (2005), 36(2):135-139 (abstract only) (Year: 2005).*
Gu et al, Preparation, Characterization, and Immunogenicity of Meningococcal Lipooligosaccharide-Derived Oligosaccharide-Protein Conjugates. Infection and Immunity, May 1993, 61/5:1873-1880 (Year: 1993).*
Agbarakwe et al., "Avidity of specific IgG antibodies elicited by immunisation against *Haemophilus influenzae* type b," *Journal of Clinical Pathology* 48(3):206-209, 1995. (5 pages).
Amir et al., "Immunogenicity and safety of a liquid combination of DT-PRP-T vs lyophilized PRP-T reconstituted with DTP," *Vaccine* 15(2):149-154, 1997.
Anderson et al., "Safety and Immunogenicity of Meningococcal A and C Polysaccharide Conjugate Vaccine in Adults," *Infection and Immunity* 62(8):3391-3395, 1994.
Anderson et al., "Safety, tolerability and immunogenicity of low dose *Haemophilus influenzae* type b conjugated to the outer membrane protein complex of *Neisseria meningitidis* group B," *The Pediatric Infectious Disease Journal* 21(4):350-352, 2002.
André, "Development and clinical application of new polyvalent combined paediatric vaccines," *Vaccine* 17(13-14):1620-1627, 1999.
Aristegui et al., "Comparison of the reactogenicity and immunogenicity of a combined diphtheria, tetanus, acellular pertussis, hepatitis B, inactivated polio (DTPa-HBV-IPV) vaccine, mixed with the *Haemophilus influenzae* type b (Hib) conjugate vaccine and administered as a single injection, with the DTPa-IPV/Hib and hepatitis B vaccines administered in two simultaneous injections to infants at 2, 4, and 6 months of age," *Vaccine* 21(25-26):3593-3600, 2003.
Avendano et al., "*Haemophilus influenzae* type b polysaccharide-tetanus protein conjugate vaccine does not depress serologic responses to diphtheria, tetanus or pertussis antigens when coadministered in the same syringe with diphtheria-tetanus-pertussis vaccine at two, four and six months of age," *The Pediatric Infectious Disease Journal* 12(8):638-643, 1993.
Baraldo et al., "N19 Polyepitope as a Carrier for Enhanced Immunogenicity and Protective Efficacy of Meningococcal Conjugate Vaccines," *Infection and Immunity* 72(8):4884-4887, 2004.
Bardotti et al., "Physicochemical characterisation of glycoconjugate vaccines for prevention of meningococcal diseases," *Vaccine* 26(18):2284-2296, 2008.
Barington et al., "Non-Epitope-Specific Suppression of the Antibody Response to *Haemophilus influenzae* Type b Conjugate Vaccines by Preimmunization with Vaccine Components.," *Infection and Immunity* 61(2):432-438, 1993. (8 pages).
Barington et al., "Opposite Effects of Actively and Passively Acquired Immunity to the Carrier on Responses of Human Infants to a *Haemophilus influenzae* Type b Conjugate Vaccine," *Infection and Immunity* 62(1):9-14, 1994. (7 pages).
Barrios et al., "Mycobacterial heat-shock proteins as carrier molecules. II: The use of the 70-kDa mycobacterial heat-shock protein as carrier for conjugated vaccines can circumvent the need for adjuvants and Bacillus Calmette Guérin priming," *European Journal of Immunology* 22(6):1365-1372, 1992.
Berry et al., "Effect of O Acetylation of *Neisseria meningitidis* Serogroup A Capsular Polysaccharide on Development of Functional Immune Responses," *Infection and Immunity* 70(7):3707-3713, 2002. (8 pages).
Bethell et al., "A Novel Method of Activation of Cross-linked Agaroses with 1,1'-Carbonyldiimidazole Which Gives a Matrix for Affinity Chromatography Devoid of Additional Charged Groups," *The Journal of Biological Chemistry* 254(8):2572-2574, 1979.
Borrow et al., "Long-term protection in children with meningococcal C conjugate vaccination: lessons teamed," *Expert Review of Vaccines* 5(6):851-857, 2006.
Bravo et al., "The new DTPw-HBV-Hib combination vaccine can be used at the WHO schedule with a monovalent dose of hepatitis B vaccine at birth," *The Southeast Asian Journal of Tropical Medicine and Public Health* 29(4):772-778, 1998.
Burrage et al., "Effect of Vaccination with Carrier Protein on Response to Meningococcal C Conjugate Vaccines and Value of Different Immunoassays as Predictors of Protection," *Infection and Immunity* 70(9):4946-4954, 2002. (10 pages).
Buttery et al., "Immunogenicity and Safety of a Combination Pneumococcal-Meningococcal Vaccine in Infants," *The Journal of the American Medical Association* 293(14): 1751-1758, 2005.
Cai et al., "LC/MS Characterization of Meningococcal Depolymerized Polysaccharide Group C Reducing Endgroup and Internal Repeating Unit," *Analytical Chemistry* 76(24):7387-7390, 2004.
Campbell et al., "Safety, Reactogenicity, and Immunogenicity of a Tetravalent Meningococcal Polysaccharide-Diphtheria Toxoid Conjugate Vaccine Given to Healthy Adults," *The Journal of Infectious Diseases* 186(12):1848-1851, 2002.
Campbell et al., "Standard and alternative regimens of *Haemophilus influenzae* type b conjugate vaccine (polyribosylribitol phosphate-tetanus toxoid conjugate vaccine) elicit comparable antibody avidities in infants," *The Pediatric Infectious Disease Journal* 21(9):822-826, 2002.
Chippaux et al., "Immunogenicity, safety, and memory of different schedules of *Neisseria meningitidis* A/C-diphtheria toxoid conjugate vaccine in infants in Niger," *Vaccine* 22(25-26):3303-3311, 2004.
Choo et al., "Immunogenicity and reactogenicity of a group C meningococcal conjugate vaccine compared with a group A + C meningococcal polysaccharide vaccine in adolescents in a randomised observer-blind controlled trial," *Vaccine* 18(24):2686-2692, 2000.
Choo et al., "Immunogenicity and reactogenicity of a pneumococcal conjugate vaccine administered combined with a *Haemophilus influenzae* type b conjugate vaccine in United Kingdom infants," *The Pediatric Infectious Disease Journal* 19(9):854-862, 2000.

(56) References Cited

OTHER PUBLICATIONS

Chu et al., "Further Studies on the Immunogenicity of *Haemophilus influenzae* Type b and Pneumococcal Type 6A Polysaccharide-Protein Conjugates," *Infection and Immunity* 40(1):245-256, 1983.
Claesson et al., "Clinical and immunologic responses to the capsular polysaccharide of *Haemophilus influenzae* type b alone or conjugated to tetanus toxoid in 18- to 23-month-old children," *The Journal of Pediatrics* 112(5):695-702, 1988.
Conterno et al., "Conjugate vaccines for preventing meningococcal C meningitis and septicaemia...," *Cochrane Database of Systematic Reviews*, vol. 3:CD001834, 2006. (Abstract Only).
Corbel, "Control Testing of Combined Vaccines: A Consideration of Potential Problems and Approaches," *Biologicals* 22(4):353-360, 1994.
Costantino et al., "Development and phase 1 clinical testing of a conjugate vaccine against meningococcus A and C," *Vaccine* 10(10):691-698, 1992.
Dagan et al., "Glycoconjugate vaccines and immune interference: A review," *Vaccine* 28(34):5513-5523, 2010.
Dagan et al., "Reduced Response to Multiple Vaccines Sharing Common Protein Epitopes That Are Administered Simultaneously to Infants," *Infection and Immunity* 66(5):2093-2098, 1998.
De Bolle et al., "The length of a tetranucleotide repeat tract in *Haemophilus influenzae* determines the phase variation rate of a gene with homology to type III DNA methyltransferases," *Molecular Microbiology* 35(1):211-222, 2000.
Drachenberg et al., "A well-tolerated grass pollen-specific allergy vaccine containing a novel adjuvant, monophosphoryl lipid A, reduces allergic symptoms after only four preseasonal injections," *Allergy* 56(6):498-505, 2001.
European Centre for Disease Prevention and Control, *Haemophilus influenzae* type b (Hib), Factsheet for health professionals, URL= http://www.ecdc.europa.eu/en/healthtopics/Haemophilus_Influenzae_Infection/basic_facts/Pages/healthprofessionals.aspx, download date Apr. 22, 2013, 3 pages.
European Medicines Agency, Announcement of Grant of Marketing Authorisation for the Prevenar Pneumococcal Conjugate Vaccine, Committee for Proprietary Medicinal Products European Public Assessment Report, 2001.
European Medicines Agency, Guideline on Adjuvants in Vaccines for Human Use, Committee for Medicinal Products for Human Use, 2005. (18 pages).
European Medicines Agency, Infanrix Hexa: EPAR—Product Information, published Nov. 26, 2008. (First Page).
Falugi et al., "Rationally designed strings of promiscuous CD4$^+$ T cell epitopes provide help to *Haemophilus influenzae* type b oligosaccharide: a model for new conjugate vaccines," *The European Journal of Immunology* 31(12):3816-3824, 2001.
Fattom et al., "Epitopic overload at the site of injection may result in suppression of the immune response to combined capsular polysaccharide conjugate vaccines," *Vaccine* 17(2):126-133, 1999.
Fernández et al., "Randomized trial of the immunogenicity of fractional dose regimens of PRP-T *Haemophilus influenzae* type b conjugate vaccine," *The American Journal of Tropical Medicine and Hygiene* 62(4):485-490, 2000.
Foster et al., "New therapies and vaccines for bacterial meningitis," *Expert Opinion on Investigational Drugs* 11(8):1051-1060, 2002.
Frasch, "Preparation of bacterial polysaccharide-protein conjugates: Analytical and manufacturing challenges," *Vaccine* 27(46):6468-6470, 2009.
Gatchalian et al., "Antibody persistence and immune memory in 10-month-old infants primed with Tritanrix™-HepB/Hib-MenAC at 6, 10, 14 weeks of age," *14$^{th}$ International Pathogenic Neisseria Conference*, Milwaukee, WI, USA, Sep. 5-10, 2004, 2 pages. (Abstract and Poster only).
Gatchalian et al., "Immunogenicity and safety of 3 doses of Tritanrix™-HepB/Hib-MenAC vaccine administered to infants at 6, 10, and 14 weeks of age," *14$^{th}$ International Pathogenic Neisseria Conference*, Milwaukee, WI, USA, Sep. 5-10, 2004, 2 pages. (Abstract and Poster only).

Gatchalian et al., "The development of a new heptavalent diphtheria-tetanus-whole cell pertussis-hepatitis B-*Haemophilus influenzae* type b-*Neisseria meningitidis* serogroups A and C vaccine: a randomized dose-ranging trial of the conjugate vaccine components," *International Journal of Infectious Diseases* 12(3):278-288, 2008.
Geyer et al., "Immunochemical Properties of Oligosaccharide-Protein Conjugates with *Klebsiella*-K2 Specificity," *Medical Microbiology and Immunology* 165(4):271-288, 1979.
Girard et al., "A review of vaccine research and development: Meningococcal disease," *Vaccine* 24(22):4692-4700, 2006.
GlaxoSmithKline, Hiberix® Consumer Medicine Information, May 16, 2011, 3 pages.
Granoff et al., "Meningococcal Polysaccharide-Protein Conjugate Vaccines," *International Journal of Infectious Diseases* 1(3):152-157, 1997.
Granoff et al., Chapter 34, "Meningococcal Vaccines," in Plotkin & Mortimer (ed.), *Vaccines*, 4$^{th}$ ed., W. B. Saunders Co., Philadelphia, 2004, pp. 959-987.
Granoff et al., "MF59 Adjuvant Enhances Antibody Responses of Infant Baboons Immunized with *Haemophilus influenzae* Type b and *Neisseria meningitidis* Group C Oligosaccharide-CRM$_{197}$ Conjugate Vaccine," *Infection and Immunity* 65(5):1710-1715, 1997.
Gupta et al., "Biodegradable Polymer Microspheres as Vaccine Adjuvants and Delivery Systems," *Developments in Biological Standardization* 92:63-78, Proceedings of Modulation of the Immune Response to Vaccine Antigens: Symposium, Bergen, Norway, Jun. 18-21, 1996.
Hearn et al., "Application of 1,1'-carbonyldiimidazole-activated matrices for the purification of proteins: III. The use of 1,1'-carbonyldiimidazole-activated agaroses in the biospecific affinity chromatographic isolation of serum antibodies," *Journal of Chromatography* 218:509-518, 1981.
Huebner et al., "Dose response of CRM$_{197}$ and tetanus toxoid-conjugated *Haemophilus influenzae* type b vaccines," *Vaccine* 23(6):802-806, 2004.
Jennings et al., "Immunochemistry of groups A, B, and C meningococcal polysaccharide-tetanus toxoid conjugates," *The Journal of Immunology* 127(3):1011-1018, 1981.
Joshi et al., "Meningococcal polysaccharide vaccines: A review," *Carbohydrate Polymers* 75(4):553-565, 2009.
Kuo et al., "Characterization of a Recombinant Pneumolysin and Its Use as a Protein Carrier for Pneumococcal Type 18C Conjugate Vaccines," *Infection and Immunity* 63(7):2706-2713, 1995.
Lagos et al., "Economisation of vaccination against *Haemophilus influenzae* type b: a randomised trial of immunogenicity of fractional-dose and two-dose regimens," *The Lancet* 351(9114):1472-1476, 1998.
Lakshman et al., "Meningococcal serogroup C conjugate vaccine," *Expert Opinion on Biological Therapy* 2(1):87-96, 2002.
Lepow, Chapter 17, "Meningococcal Vaccines," in Plotkin & Mortimer (ed.), *Vaccines*, 2$^{nd}$ ed., W. B. Saunders Co., Philadelphia, 1994, pp. 503-515. (16 pages).
Lowry et al., "Protein measurement with the folin phenol reagent," *The Journal of Biological Chemistry* 193(1):265-275, 1951.
MacLennan et al., "Safety, Immunogenicity, and Induction of Immunologic Memory by a Serogroup C Meningococcal Conjugate Vaccine in Infants: A Randomized Controlled Trial," *The Journal of the American Medical Association* 283(21):2795-2801, 2000.
Mendelman et al., "Immunogenicity and safety of *Haemophilus influenzae* type b polysaccharide-*Neisseria meningitidis* conjugate vaccine in 7.5 µg liquid formulation: a comparison of three lots with the 15.0 µg lyophilized formulation," *Vaccine* 15(6-7):775-781, 1997.
Molrine et al., "Antibody Responses to Polysaccharide and Polysaccharide-Conjugate Vaccines after Treatment of Hodgkin Disease," *Annals of Internal Medicine* 123(11):828-834, 1995.
Monsigny et al., "Colorimetric Determination of Neutral Sugars by a Resorcinol Sulfuric Acid Micromethod," *Analytical Biochemistry* 175(2):525-530, 1988.
Nicol et al., "*Haemophilus influenzae* type b conjugate vaccine diluted tenfold in diphtheria-tetanus-whole cell pertussis vaccine: a randomized trial," *The Pediatric Infectious Disease Journal* 21(2):138-141, 2002. (8 pages).

(56) References Cited

OTHER PUBLICATIONS

Nolan et al., "A novel combined *Haemophilus influenzae* type b-*Neisseria meningitidis* serogroups C and Y-tetanus-toxoid conjugate vaccine is immunogenic and induces immune memory when co-administered with DTPa-HBV-IPV and conjugate pneumococcal vaccines in infants," *Vaccine* 25(51):8487-8499, 2007.
Obaro et al., "Safety and immunogenicity of pneumococcal conjugate vaccine in combination with diphtheria, tetanus toxoid, pertussis and *Haemophilus influenzae* type b conjugate vaccine," *The Pediatric Infectious Disease Journal* 21(10):940-946, 2002. (8 pages).
Papaevangelou, "Current combined vaccines with hepatitis B," *Vaccine* 16(Supplement 1):S69-S72, 1998.
Paradiso et al., "Glycoconjugate Vaccines: Future Combinations," *Developments in Biological Standardization* 87:269-275, Proceedings of New Approaches to Stabilisation of Vaccines Potency, Geneva, Switzerland, May 29-31, 1995. (4 pages).
Paradiso et al., "Introduction to Combination Vaccines," Abstract S15, $1^{st}$ *Annual Conference on Vaccine Research*, Washington D.C., USA, May 30-Jun. 1, 1998.
Pasteur Mérieux Connaught, "Haemophilus b Conjugate Vaccine (Tetanus Toxoid Conjugate) ActHIB®," Product Information, A.H. F.S. Category 80:12, 1996.
Peeters et al., "Effect of Carrier Priming on Immunogenicity of Saccharide-Protein Conjugate Vaccines," *Infection and Immunity* 59(10):3504-3510, 1991. (8 pages).
Perkins, "New Opportunities for Prevention of Meningococcal Disease," *The Journal of the American Medical Association* 283(21):2842-2843, 2000. (3 pages).
Peterson, "Review of the Folin Phenol Protein Quantitation Method of Lowry, Rosebrough, Farr and Randall," *Analytical Biochemistry* 100(2):201-220, 1979.
Pines et al., "New acellular pertussis-containing paediatric combined vaccines," *Vaccine* 17(13- 14):1650-1656, 1999. (8 pages).
Plotkin et al. (ed.), *Vaccines*, $3^{rd}$ ed., W. B. Saunders Co., Philadelphia, 1999, pp. 200-202. (5 pages).
Poland, "The burden of pneumococcal disease: the role of conjugate vaccines," *Vaccine* 17(13- 14):1674-1679, 1999.
Pollabauer et al., "The influence of carrier protein on the immunogenicity of simultaneously administered conjugate vaccines in infants," *Vaccine* 27(11):1674-1679, 2009.
Rappuoli, "Conjugates and reverse vaccinology to eliminate bacterial meningitis," *Vaccine* 19(17-19):2319-2322, 2001.
Rappuoli et al., "New vaccines, especially new combined vaccines," Report of the Expert Panel VIII, European Commission Cost/STD Initiative, *Vaccine* 14(7):691-700, 1996.
Rennels et al., "Dose escalation, safety and immunogenicity study of a tetravalent meningococcal polysaccharide diphtheria conjugate vaccine in toddlers," *The Pediatric Infectious Disease Journal* 21(10):978-979, 2002.
Rennels et al., "Safety and Immunogenicity of Combined Conjugate 9-Valent *S. pneumoniae*-meningococcal group C (9vPnC-MnCC) and *H. influenza* b-9vPnC-MnCC (HbOC-9vPnC-MnCC) Vaccine," Abstract G-2039, $41^{st}$ *Interscience Conference of Antimicrobial Agents and Chemotherapy*, Chicago, IL, USA, Dec. 16-19, 2001, 1 page.
Rennels et al., "Safety and Immunogenicity of Heptavalent Pneumococcal Vaccine Conjugated to $CRM_{197}$ in United States Infants," *Pediatrics* 101(4):604-611, 1998. (10 pages).
Richmond et al., "Evaluation of De-O-Acetylated Meningococcal C Polysaccharide-Tetanus Toxoid Conjugate Vaccine in Infancy: Reactogenicity, Immunogenicity, Immunologic Priming, and Bactericidal Activity against O-Acetylated and De-O-Acetylated Serogroup C Strains," *Infection and Immunity* 69(4):2378-2382, 2001.
Richmond et al., "Meningococcal Serogroup C Conjugate Vaccine is Immunogenic in Infancy and Primes for Memory," *The Journal of Infectious Diseases* 179(6):1569-1572, 1999.
Richmond et al., "Safety and immunogenicity of a new *Neisseria meningitidis* serogroup C-tetanus toxoid conjugate vaccine in healthy adults," *Vaccine* 18(7-8):641-646, 2000.

Romero-Steiner et al., "Functional Antibody Activity Elicited by Fractional Doses of *Haemophilus influenzae* Type b Conjugate Vaccine (Polyribosylribitol Phosphate-Tetanus Toxoid Conjugate)," *Clinical and Diagnostic Laboratory Immunology* 8(6):1115-1119, 2001.
Schneerson et al., "Quantitative and Qualitative Analyses of Serum Antibodies Elicited in Adults by Haemophilus influenzae Type b and Pneumococcus Type 6A Capsular Polysaccharide-Tetanus Toxoid Conjugates," *Infection and Immunity* 52(2):519-528, 1986. (11 pages).
Siber et al., "Development of a guinea pig model to assess immunogenicity of *Haemophilus influenzae* type b capsular polysaccharide conjugate vaccines," *Vaccine* 13(6):525-531, 1995.
Silveira et al., "Characterization and immunogenicity of meningococcal group C conjugate vaccine prepared using hydrazide-activated tetanus toxoid," *Vaccine* 25(41):7261-7270, 2007.
Snape et al., "Meningococcal polysaccharide-protein conjugate vaccines," *The Lancet Infectious Diseases* 5(1):21-30, 2005.
Sood et al., "Capsular polysaccharide-protein conjugate vaccines," *Drug Discovery Today* 1(9):381-387, 1996.
Takahashi et al., "Induction of $CD8^+$ cytotoxic T cells by immunization with purified HIV-1 envelope protein in ISCOMs," *Nature* 344(6269):873-875, 1990.
Tamm et al., "Double-blind study comparing the immunogenicity of a licensed DTwPHib-CRM197 conjugate vaccine (Quattvaxem™) with three investigational, liquid formulations using lower doses of Hib-CRM197 conjugate," *Vaccine* 23(14):1715-1719, 2005.
Tan, "Pneumococcal conjugate vaccines—implications for community antibiotic prescribing," *Current Opinion in Microbiology* 3(5):502-507, 2000.
Uchida et al., "Diphtheria Toxin and Related Proteins," *The Journal of Biological Chemistry* 248(11):3838-3844, 1973.
Ugozzoli et al., "Combinations of Protein Polysaccharide Conjugate Vaccines for Intranasal Immunization," *The Journal of Infectious Diseases* 186(9):1358-1361, 2002.
Van der Meeren et al., "Phospholipid composition of r-DNA hepatitis B surface antigens," *International Journal of Pharmaceutics* 106(1):89-92, 1994.
Vanlandschoot et al., "*Saccharomyces cerevisiae*-Derived HBsAg Preparations Differ in Their Attachment to Monocytes, Immune-Suppressive Potential, and T-Cell Immunogenicity," *Journal of Medical Virology* 70(4):513-519, 2003.
von Hunolstein et al., "Synthetic oligodeoxynucleotide containing CpG motif induces an anti-polysaccharide type 1-like immune response after immunization of mice with *Haemophilus influenzae* type b conjugate vaccine," *International Immunology* 12(3):295-303, 2000. (10 pages).
Ward et al., Chapter 12, "*Haemophilus influenzae* vaccines," in Plotkin & Mortimer (ed.), *Vaccines*, $2^{nd}$ ed., W. B. Saunders Co., Philadelphia, 1994, pp. 337-386. (53 pages).
Watemberg et al., "Safety and immunogenicity of *Haemophilus* type b-tetanus protein conjugate vaccine, mixed in the same syringe with diphtheria-tetanus-pertussis vaccine in young infants," *The Pediatric Infectious Disease Journal* 10(10):758-763, 1991.
Wyeth (N.Z.) Limited, Tetramune®, Approved Data Sheet, URL= http://www.ias.org.nz/tetramune.htm, download date Apr. 12, 2003, 10 pages.
Wyeth Lederle Vaccines S.A., Scientific Discussion, Marketing Authorization Application for the Prevenar Pneumococcal Conjugate Vaccine, 2000, 34 pages.
Zangwill et al., "Safety and immunogenicity of a heptavalent pneumococcal conjugate vaccine in infants," *Vaccine* 21(17-18):1894-1900, 2003. (8 pages).
Zepp et al., "Evidence for induction of polysaccharide specific B-cell-memory in the 1st year of life: plain *Haemophilus influenzae* type b—PRP (Hib) boosters children primed with a tetanus-conjugate Hib-DTPa-HBV combined vaccine," *European Journal of Pediatrics* 156(1):18-24, 1997.
Zimmer et al., "Meningococcal conjugate vaccines," *Expert Opinion on Pharmacotherapy* 5(4):855-863, 2004.

* cited by examiner

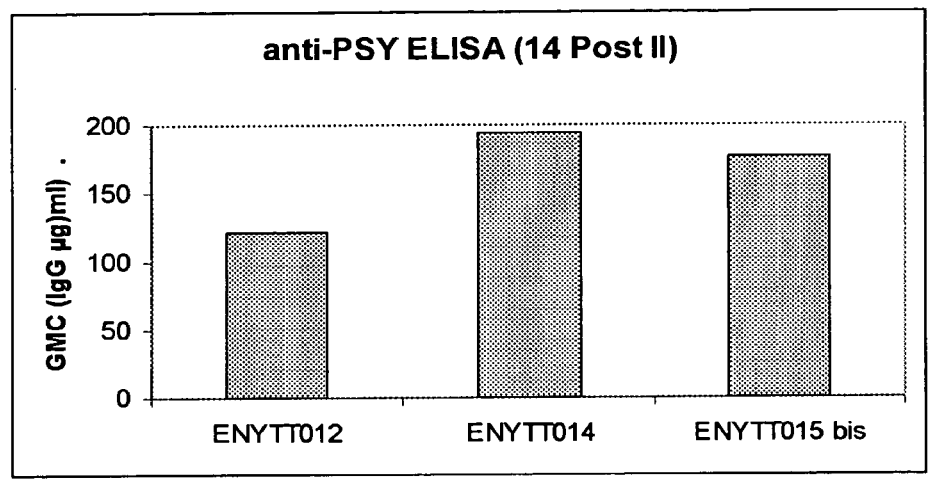
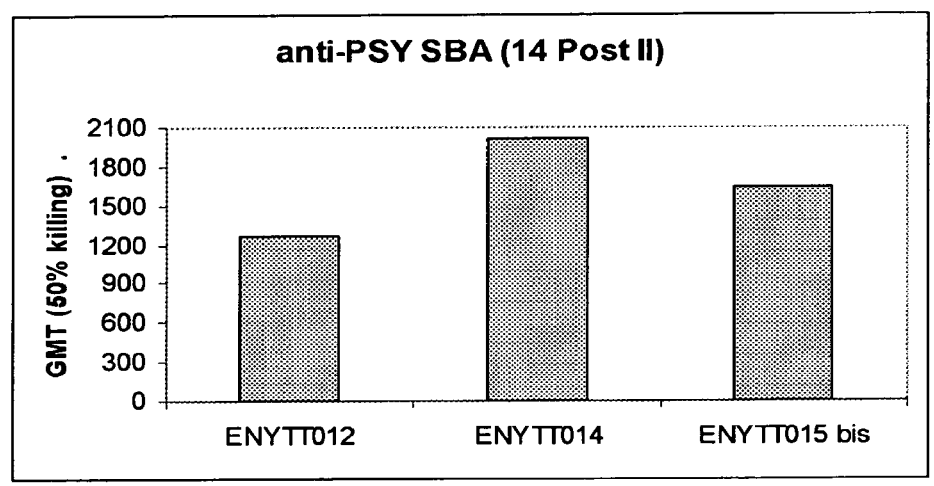

IMMUNOGENIC COMPOSITION

The present invention relates to immunogenic compositions comprising bacterial capsular saccharides conjugated to a carrier protein, in particular those saccharides of *N. meningitidis*. It additionally relates to vaccines and vaccine kits comprising such saccharide conjugates, processes for making the immunogenic compositions and vaccines and the use of the vaccines and immunogenic compositions of the invention in therapy. It also relates to methods of immunising against infection using the saccharide conjugates and the use of the saccharide conjugates in the manufacture of a medicament.

*Neisseria meningitidis* is a Gram-negative human pathogen which causes bacterial meningitis. Based on the organism's capsular polysaccharide, twelve serogroups of *N. meningitidis* have been identified (A, B, C, H, I, K, L, 29E, W135, X, Y and Z). Serogroup A (MenA) is the most common cause of epidemic disease in sub-Saharan Africa. Serogroups B and C are responsible for the majority of cases in developing countries, with the remaining cases being caused by W135 and Y).

Immunogenic compositions comprising *N. meningitidis* saccharides conjugated to carrier proteins are known in the art; the carrier protein having the known effect of turning the T-independent polysaccharide antigen into a T-dependent antigen capable of triggering an immune memory response. For instance WO 02/58737 discloses a vaccine comprising purified capsular polysaccharides from *N. meningitidis* serogroups A, C, W135 and Y conjugated to a carrier protein. However, this application teaches that all polysaccharides should essentially be conjugated in the same way (through the same linker to the same protein carrier).

There remains a need to develop improved conjugate vaccines against neisserial meningitis. The present invention concerns the provision of a meningococcal polysaccharide conjugate vaccine where conjugation of each polysaccharide is tailored (rather than being uniform) to achieve an efficacious combination vaccine.

In particular it is advantageous to use linker molecules to conjugate certain meningococcal saccharides to their protein carriers in combination with others that are directly conjugated. In this way polysaccharides that are less good immunogens may be presented to the immune system via a linker, and those that are very good immunogens may be directly conjugated so that they do not dominate the immune response to the combination.

Accordingly, in one aspect of the present invention there is provided an immunogenic composition comprising at least 2 different *N. meningitidis* capsular saccharides, wherein one or more is/are selected from a first group consisting of MenA, MenC, MenY and MenW which is/are conjugated through a linker to a carrier protein(s), and one or more different saccharides is/are selected from a second group consisting of MenA, MenC, MenY and MenW which is/are directly conjugated to a carrier protein(s).

In a MenAC vaccine, for example, MenA may be conjugated through a linker and MenC directly. In a MenCY vaccine, MenC may be conjugated through a linker and MenY directly. In a MenACWY vaccine Men A may be conjugated through a linker and MenCWY directly, or MenAC may be conjugated through a linker and MenWY directly.

A further consideration in a combination vaccine comprising various saccharides conjugated to the same carrier is the issue of carrier immune suppression: too much carrier may be used and the immune response may be dampened. With a uniform approach to conjugation the carrier will present a similar blend of B- and T-cell epitopes to the immune system. However if conjugation takes place at different chemical groups within the carrier protein for one saccharide versus another, the protein carriers are likely to be different to some extent in how they present themselves to the immune system.

Accordingly, in a separate embodiment of the invention there is provided an immunogenic composition comprising at least 2 different saccharides conjugated separately to the same type of carrier protein (for instance tetanus toxoid), wherein one or more saccharide(s) is/are conjugated to the carrier protein via a first type of chemical group on the protein carrier, and one or more saccharide(s) is/are conjugated to the carrier protein via a second (different) type of chemical group on the protein carrier.

The first and second types of chemical group may be present in the protein carrier on a mutually exclusive first and second set of amino acids of the protein carrier (for instance certain aspartic acid/glutamic acid residues in one set and certain lysine residues in the second). One saccharide may be conjugated to a carboxyl group on the carrier, and another on an amino group for instance. Such conjugation may involve conjugation on separate B- and/or T-cell epitopes for each different conjugate.

For instance in a MenAC vaccine, MenA may be linked to a first type of chemical group (such as carboxyl) on the carrier protein and MenC linked to a second (such as amino). In a MenCY vaccine MenC may be linked to a first type of chemical group (such as carboxyl) on the carrier protein and MenY linked to a second (such as amino). In a MenACWY vaccine, MenAC may be linked to a first type of chemical group (such as carboxyl) on the carrier protein and MenWY linked to a second (such as amino), or MenA may be linked to a first type of chemical group (such as carboxyl) on the carrier protein and MenCWY linked to a second (such as amino).

According to a further aspect of the invention there is provided a method of immunising a human host against disease caused by *Neisseria meningitidis* comprising administering to the host an immunoprotective dose of the immunogenic composition or vaccine of the invention.

According to a further aspect or the invention there is provided an immunogenic composition of the invention for use in the treatment or prevention of disease caused by *Neisseria meningitidis*.

According to a further aspect or the invention there is provided a use of the immunogenic composition or vaccine of the invention in the manufacture of a medicament for the treatment or prevention of diseases caused by *Neisseria meningitidis*.

DESCRIPTION OF FIGURES

FIG. 1—A—Bar chart showing GMC responses in an anti-MenY ELISA. ENYTT012 is a MenY-TT conjugate prepared from native MenY polysaccharide. ENYTT014 is a MenY-TT conjugate prepared from microfluidised MenY polysaccharide which had undergone 40 cycles of microfluidisation. ENYTT015bis is a MenY-TT conjugate prepared from microfluidised MenY polysaccharide which had undergone 20 cycles of microfluidisation.

B—Bar chart showing GMT responses in an anti-MenY SBA assay. ENYTT012 is a MenY-TT conjugate prepared from native MenY polysaccharide. ENYTT014 is a MenY-TT conjugate prepared from microfluidised MenY polysaccharide which had undergone 40 cycles of microfluidisation.

ENYTT015bis is a MenY-TT conjugate prepared from microfluidised MenY polysaccharide which had undergone 20 cycles of microfluidisation.

DETAILED DESCRIPTION

In one aspect of the present invention there is provided an immunogenic composition comprising at least 2 different *N. meningitidis* capsular saccharides, wherein one or more is/are selected from a first group consisting of MenA, MenC, MenY and MenW which is/are conjugated through a linker to a carrier protein(s), and one or more different saccharides is/are selected from a second group consisting of MenA, MenC, MenY and MenW which is/are directly conjugated to a carrier protein(s).

More specifically, the first group may consist of MenA and MenC, and the second group consist of MenC, MenY and MenW. Particular embodiments of the invention are immunogenic compositions comprising: MenA capsular saccharide conjugated through a linker to a carrier protein and MenC capsular saccharide directly conjugated to a carrier protein; MenC capsular saccharide conjugated through a linker to a carrier protein and MenY capsular saccharide directly conjugated to a carrier protein; MenA and MenC capsular saccharides conjugated through a linker to a carrier protein(s) and MenY and Men W capsular saccharides directly conjugated to a carrier protein(s); MenA capsular saccharide conjugated through a linker to a carrier protein and MenC, MenY and Men W capsular saccharides directly conjugated to a carrier protein(s). In any of these embodiments a Hib conjugate may also be included, which is linked to a carrier protein (see list of carriers above and below, for example TT) directly or through a linker.

The term "saccharide" throughout this specification may indicate polysaccharide or oligosaccharide and includes both. Polysaccharides are isolated from bacteria or isolated from bacteria and sized to some degree by known methods (see for example EP497524 and EP497525) and optionally by microfluidisation. Polysaccharides can be sized in order to reduce viscosity in polysaccharide samples and/or to improve filterability for conjugated products. Oligosaccharides have a low number of repeat units (typically 5-30 repeat units) and are typically hydrolysed polysaccharides.

Each *N. meningitidis* (and/or Hib) capsular saccharide may be conjugated to a carrier protein independently selected from the group consisting of TT, DT, CRM197, fragment C of TT and protein D. A more complete list of protein carriers that may be used in the conjugates of the invention is presented below. Although one or more *N. meningitidis* (and/or Hib) capsular saccharide may be conjugated to different carrier proteins from the others, in one embodiment they are all conjugated to the same carrier protein. For instance they may all be conjugated to the same carrier protein selected from the group consisting of TT, DT, CRM197, fragment C of TT and protein D. In this context CRM197 and DT may be considered to be the same carrier protein as they differ by only one amino acid. In an embodiment all the *N. meningitidis* (and/or Hib) capsular saccharides present are conjugated to TT.

If the protein carrier is the same for 2 or more saccharides in the composition, the saccharide could be conjugated to the same molecule of the protein carrier (carrier molecules having 2 more different saccharides conjugated to it) [see for instance WO 04/083251; for example, a single carrier protein might be conjugated to MenA and MenC; MenA and MenW; MenA and MenY; MenC and MenW; MenC and MenY; Men W and MenY; MenA, MenC and MenW; MenA, MenC and MenY; MenA, MenW and MenY; MenC, MenW and MenY; MenA, MenC, MenW and MenY; Hib and MenA; Hib and MenC; Hib and MenW; or Hib and MenY]. Alternatively the saccharides may each be separately conjugated to different molecules of the protein carrier (each molecule of protein carrier only having one type of saccharide conjugated to it).

Immunogenic compositions of the first aspect of the invention may also have any or all the additional characteristics of the second aspect of the invention and vice versa.

In a second aspect of the invention there is presented an immunogenic composition comprising at least 2 different saccharide conjugates conjugated separately to the same type of carrier protein, wherein one or more saccharide(s) is/are conjugated to the carrier protein via a first type of chemical group on the protein carrier, and one or more saccharide(s) is/are conjugated to the carrier protein via a second (different) type of chemical group on the protein carrier.

In one embodiment the 2 conjugates involve the same saccharide linked to the same carrier, but by different conjugation chemistries. In an alternative embodiment 2 different saccharides are conjugated to different groups on the protein carrier.

By "conjugated separately to the same type of carrier protein" it is meant that the saccharides are conjugated to the same carrier individually (for example, MenA is conjugated to tetanus toxoid through an amine group on the tetanus toxoid and MenC is conjugated to tetanus toxoid through a carboxylic acid group on a different molecule of tetanus toxoid.)

The capsular saccharide(s) may be conjugated to the same carrier protein independently selected from the group consisting of TT, DT, CRM197, fragment C of TT and protein D. A more complete list of protein carriers that may be used in the conjugates of the invention is presented below. In this context CRM197 and DT may be considered to be the same carrier protein as they differ by only one amino acid. In an embodiment all the capsular saccharides present are conjugated to TT.

In one embodiment the first and second type of chemical group on the protein carrier are present on separate B- and/or T-cell epitopes on the carrier protein. That is, they are present on a different set of B- and/or T-cell epitopes from each other. To predict B-cell epitopes for a carrier known methods may be used such as either or both of the following two methods: 2D-structure prediction and/or antigenic index prediction. 2D-structure prediction can be made using the PSIPRED program (from David Jones, Brunel Bioinformatics Group, Dept. Biological Sciences, Brunel University, Uxbridge UB8 3PH, UK). The antigenic index can be calculated on the basis of the method described by Jameson and Wolf (CABIOS 4:181-186 [1988]). The parameters used in this program are the antigenic index and the minimal length for an antigenic peptide. An antigenic index of 0.9 for a minimum of 5 consecutive amino acids can be used as the thresholds in the program. T-helper cell epitopes are peptides bound to HLA class II molecules and recognized by T-helper cells. The prediction of useful T-helper cell epitopes can be based on known techniques, such as the TEPITOPE method describe by Sturniolo at al. (Nature Biotech. 17: 555-561 [1999]).

The saccharides may be selected from a group consisting of: *N. meningitidis* serogroup A capsular saccharide (MenA), *N. meningitidis* serogroup C capsular saccharide (MenC), *N. meningitidis* serogroup Y capsular saccharide (MenY), *N. meningitidis* serogroup W capsular saccharide (MenW), *H.*

*influenzae* type b capsular saccharide (Hib), Group B *Streptococcus* group I capsular saccharide, Group B *Streptococcus* group II capsular saccharide, Group B *Streptococcus* group III capsular saccharide, Group B *Streptococcus* group IV capsular saccharide, Group B *Streptococcus* group V capsular saccharide, *Staphylococcus aureus* type 5 capsular saccharide, *Staphylococcus aureus* type 8 capsular saccharide, Vi saccharide from *Salmonella typhi*, *N. meningitidis* LPS (such as L3 and/or L2), *M. catarrhalis* LPS, *H. influenzae* LPS, and from any of the capsular pneumococcal saccharides such as from serotype: 1, 2, 3, 4, 5, 6A, 6B, 7F, 8, 9N, 9V, 10A, 11A, 12F, 14, 15B, 17F, 18C, 19A, 19F, 20, 22F, 23F or 33F. In one embodiment the immunogenic composition of the invention consists of or comprises two or more different saccharides from the same genus of bacteria (e.g. *Neisseria, Streptococcus, Staphylococcus*, or *Haemophilus*).

The first and second chemical groups present on the protein carrier are different from each other and are ideally natural chemical groups that may be readily used for conjugation purposes. They may be selected independently from the group consisting of: carboxyl groups, amino groups, sulphydryl groups, Hydroxyl groups, Imidazolyl groups, Guanidyl groups, and Indolyl groups. In one embodiment the first chemical group is carboxyl and the second is amino, or vice versa. These groups are explained in greater detail below.

In a specific embodiment the immunogenic composition comprises at least 2 different *N. meningitidis* capsular saccharides, wherein one or more is/are selected from a first group consisting of MenA and MenC which is/are conjugated to the carrier protein via the first type of chemical group on the protein carrier (for instance carboxyl), and one or more different saccharides is/are selected from a second group consisting of MenC, MenY and MenW which is/are conjugated to the carrier protein via the second type of chemical group on the protein carrier (for instance amino).

In a further embodiment the immunogenic composition of the invention comprises MenA conjugated via the first type of chemical group (for instance carboxyl), and MenC conjugated via the second type of chemical group (for instance amino).

In another embodiment the immunogenic composition comprises MenC conjugated via the first type of chemical group (for instance carboxyl), and MenY conjugated via the second type of chemical group (for instance amino).

In another embodiment the immunogenic composition comprises MenA conjugated via the first type of chemical group (for instance carboxyl), and MenC, MenY and MenW conjugated via the second type of chemical group (for instance amino).

In another embodiment the immunogenic composition comprises MenA and MenC conjugated via the first type of chemical group (for instance carboxyl), and MenY and MenW conjugated via the second type of chemical group (for instance amino).

In any of the above embodiments Hib may also be present also conjugated to the same type of protein carrier. Hib may be conjugated to the carrier by the first or second type of chemical group. In one embodiment it is conjugated via a carboxyl group.

General Considerations in the Aspects of the Invention

The saccharides of the invention (in particular the *N. meningitidis* saccharides and/or the Hib capsular saccharide) included in pharmaceutical (immunogenic) compositions of the invention are conjugated to a carrier protein such as tetanus toxoid (TT), tetanus toxoid fragment C, non-toxic mutants of tetanus toxin [note all such variants of TT are considered to be the same type of carrier protein for the purposes of this invention], diphtheria toxoid (DT), CRM197, other non-toxic mutants of diphtheria toxin [such as CRM176, CRM 197, CRM228, CRM 45 (Uchida et al J. Biol. Chem. 218; 3838-3844, 1973); CRM 9, CRM 45, CRM102, CRM 103 and CRM107 and other mutations described by Nicholls and Youle in Genetically Engineered Toxins, Ed: Frankel, Maecel Dekker Inc, 1992; deletion or mutation of Glu-148 to Asp, Gln or Ser and/or Ala 158 to Gly and other mutations disclosed in U.S. Pat. No. 4,709,017 or U.S. Pat. No. 4,950,740; mutation of at least one or more residues Lys 516, Lys 526, Phe 530 and/or Lys 534 and other mutations disclosed in U.S. Pat. No. 5,917,017 or U.S. Pat. No. 6,455,673; or fragment disclosed in U.S. Pat. No. 5,843,711] (note all such variants of DT are considered to be the same type of carrier protein for the purposes of this invention), pneumococcal pneumolysin (Kuo et al (1995) Infect Immun 63; 2706-13), OMPC (meningococcal outer membrane protein—usually extracted from *N. meningitidis* serogroup B—EP0372501), synthetic peptides (EP0378881, EPO427347), heat shock proteins (WO 93/17712, WO 94/03208), pertussis proteins (WO 98/58668, EPO471177), cytokines, lymphokines, growth factors or hormones (WO 91/01146), artificial proteins comprising multiple human CD4+ T cell epitopes from various pathogen derived antigens (Falugi et al (2001) Eur J Immunol 31; 3816-3824) such as N19 protein (Baraldoi et al (2004) Infect Immun 72; 4884-7) pneumococcal surface protein PspA (WO 02/091998), iron uptake proteins (WO 01/72337), toxin A or B of *C. difficile* (WO 00/61761) or Protein D (EP594610 and WO 00/56360).

In an embodiment, the immunogenic composition of the invention uses the same type of carrier protein (independently) in at least two, three, four or each of the saccharides (e.g. *N. meningitidis* capsular saccharides and/or Hib) contained therein. In an embodiment where Hib and *N. meningitidis* capsular saccharides are present, Hib may be conjugated to the same type of carrier protein as the at least two, three, four or each of the *N. meningitidis* saccharides. For example, 2, 3 or 4 of the *N. meningitidis* saccharides (MenA,C,Y,W) are independently conjugated to tetanus toxoid to make 2, 3 or 4 conjugates, and optionally Hib is also conjugated to TT.

In an embodiment, the immunogenic composition of the invention comprises a *N. meningitidis* saccharide conjugated to a carrier protein selected from the group consisting of TT, DT, CRM197, fragment C of TT and protein D. In an embodiment, the immunogenic composition of the invention comprises a Hib saccharide conjugated to a carrier protein selected from the group consisting of TT, DT, CRM197, fragment C of TT and protein D.

The immunogenic composition of the invention optionally comprises at least one meningococcal saccharide (for example MenA; MenC; MenW; MenY; MenA and MenC; MenA and MenW; MenA and MenY; MenC and Men W; Men C and MenY; Men W and MenY; MenA, MenC and MenW; MenA, MenC and MenY; MenA, MenW and MenY; MenC, MenW and MenY or MenA, MenC, MenW and MenY) conjugate having a ratio of Men saccharide to carrier protein of between 1:5 and 5:1, between 1:2 and 5:1, between 1:0.5 and 1:2.5 or between 1:1.25 and 1:2.5 (w/w).

The immunogenic composition of the invention optionally comprises a Hib saccharide conjugate having a ratio of Hib to carrier protein of between 1:5 and 5:1; 1:2 and 2:1; 1:1 and 1:4; 1:2 and 1:3.5; or around or exactly 1:2.5 or 1:3 (w/w).

The ratio of saccharide to carrier protein (w/w) in a conjugate may be determined using the sterilized conjugate. The amount of protein is determined using a Lowry assay (for example Lowry et al (1951) J. Biol. Chem. 193, 265-275 or Peterson et al Analytical Biochemistry 100, 201-220 (1979)) and the amount of saccharide is determined using ICP-OES (inductively coupled plasma-optical emission spectroscopy) for MenA, DMAP assay for MenC and Resorcinol assay for MenW and MenY (Monsigny et al (1988) Anal. Biochem. 175, 525-530).

In an embodiment, the immunogenic composition of the invention comprises N. meningitidis saccharide conjugate(s) and/or the Hib saccharide conjugate wherein the N. meningitidis saccharide(s) and/or the Hib saccharide is conjugated to the carrier protein via a linker, for instance a bifunctional linker. The linker is optionally heterobifunctional or homobifunctional, having for example a reactive amino group and a reactive carboxylic acid group, 2 reactive amino groups or two reactive carboxylic acid groups. The linker has for example between 4 and 20, 4 and 12, 5 and 10 carbon atoms. A possible linker is ADH. Other linkers include B-propionamido (WO 00/10599), nitrophenyl-ethylamine (Geyer et al (1979) Med. Microbiol. Immunol. 165; 171-288), haloalkyl halides (U.S. Pat. No. 4,057,685), glycosidic linkages (U.S. Pat. No. 4,673,574, U.S. Pat. No. 4,808,700), hexane diamine and 6-aminocaproic acid (U.S. Pat. No. 4,459,286).

The saccharide conjugates present in the immunogenic compositions of the invention may be prepared by any known coupling technique. The conjugation method may rely on activation of the saccharide with 1-cyano-4-dimethylamino pyridinium tetrafluoroborate (CDAP) to form a cyanate ester. The activated saccharide may thus be coupled directly or via a spacer (linker) group to an amino group on the carrier protein. For example, the spacer could be cystamine or cysteamine to give a thiolated polysaccharide which could be coupled to the carrier via a thioether linkage obtained after reaction with a maleimide-activated carrier protein (for example using GMBS) or a holoacetylated carrier protein (for example using iodoacetimide or N-succinimidyl bromoacetatebromoacetate). Optionally, the cyanate ester (optionally made by CDAP chemistry) is coupled with hexane diamine or ADH and the amino-derivatised saccharide is conjugated to the carrier protein using using carbodiimide (e.g. EDAC or EDC) chemistry via a carboxyl group on the protein carrier. Such conjugates are described in PCT published application WO 93/15760 Uniformed Services University and WO 95/08348 and WO 96/29094.

Other suitable techniques use carbiinides, hydrazides, active esters, norborane, p-nitrobenzoic acid, N-hydroxysuccinimide, S-NHS, EDC, TSTU. Many are described in WO 98/42721. Conjugation may involve a carbonyl linker which may be formed by reaction of a free hydroxyl group of the saccharide with CDI (Bethell et al J. Biol. Chem. 1979, 254; 2572-4, Hearn et al J. Chromatogr. 1981. 218; 509-18) followed by reaction of with a protein to form a carbamate linkage. This may involve reduction of the anomeric terminus to a primary hydroxyl group, optional protection/deprotection of the primary hydroxyl group' reaction of the primary hydroxyl group with CDI to form a CDI carbamate intermediate and coupling the CDI carbamate intermediate with an amino group on a protein.

The conjugates can also be prepared by direct reductive amination methods as described in U.S. Pat. No. 4,365,170 (Jennings) and U.S. Pat. No. 4,673,574 (Anderson). Other methods are described in EP-0-161-188, EP-208375 and EP-0-477508.

A further method involves the coupling of a cyanogen bromide (or CDAP) activated saccharide derivatised with adipic acid hydrazide (ADH) to the protein carrier by Carbodiimide condensation (Chu C. et al Infect. Immunity, 1983 245 256), for example using EDAC.

In an embodiment, a hydroxyl group (optionally an activated hydroxyl group for example a hydroxyl group activated by a cyanate ester) on a saccharide is linked to an amino or carboxylic group on a protein either directly or indirectly (through a linker). Where a linker is present, a hydroxyl group on a saccharide is optionally linked to an amino group on a linker, for example by using CDAP conjugation. A further amino group in the linker for example ADH) may be conjugated to a carboxylic acid group on a protein, for example by using carbodiimide chemistry, for example by using EDAC. In an embodiment, the Hib or N. meningitidis capsular saccharide(s) (or saccharide in general) is conjugated to the linker first before the linker is conjugated to the carrier protein. Alternatively the linker may be conjugated to the carrier before conjugation to the saccharide.

In general the following types of chemical groups on a protein carrier can be used for coupling/conjugation:

A) Carboxyl (for instance via aspartic acid or glutamic acid). In one embodiment this group is linked to amino groups on saccharides directly or to an amino group on a linker with carbodiimide chemistry e.g. with EDAC.

B) Amino group (for instance via lysine). In one embodiment this group is linked to carboxyl groups on saccharides directly or to a carboxyl group on a linker with carbodiimide chemistry e.g. with EDAC. In another embodiment this group is linked to hydroxyl groups activated with CDAP or CNBr on saccharides directly or to such groups on a linker; to saccharides or linkers having an aldehyde group; to saccharides or linkers having a succinimide ester group.

C) Sulphydryl (for instance via cysteine). In one embodiment this group is linked to a bromo or chloro acetylated saccharide or linker with maleimide chemistry. In one embodiment this group is activated/modified with bis diazobenzidine.

D) Hydroxyl group (for instance via tyrosine). In one embodiment this group is activated/modified with bis diazobenzidine.

E) Imidazolyl group (for instance via histidine). In one embodiment this group is activated/modified with bis diazobenzidine.

F) Guanidyl group (for instance via arginine).

G) Indolyl group (for instance via tryptophan).

On a saccharide, in general the following groups can be used for a coupling: OH, COOH or NH2. Aldehyde groups can be generated after different treatments known in the art such as: periodate, acid hydrolysis, hydrogen peroxide, etc.

Direct Coupling Approaches:
Saccharide-OH+CNBr or CDAP---->cyanate ester+NH2-Prot---->conjugate
Saccharide-aldehyde+NH2-Prot---->Schiff base+NaCNBH3---->conjugate
Saccharide-COOH+NH2-Prot+EDAC---->conjugate
Saccharide-NH2+COOH-Prot+EDAC---->conjugate
Indirect Coupling Via Spacer (Linker) Approaches:
Saccharide-OH+CNBr or CDAP--->cyanate ester+NH2----NH2---->saccharide----NH2+COOH-Prot+EDAC---->conjugate Saccharide-OH+CNBr or CDAP---->cyanate ester+NH2 SH------>saccharide----SH+SH-Prot (native Protein with an exposed cysteine or obtained after modification of amino groups of the protein by SPDP for instance)---->saccharide-S-S-Prot Saccharide-OH+CNBr or CDAP--->cyanate ester+NH2----SH saccharide----SH+maleimide-Prot (modification of amino groups)---->conjugate Saccharide-COOH+EDAC+NH2 NH2--->saccharide NH2+EDAC+COOH-Prot---->conjugate Saccharide-COOH+EDAC+NH2----SH---->saccharide----SH+SH-Prot (native Protein with an exposed cysteine or obtained after modification of amino groups of the protein by SPDP for instance)----->saccharide-S-S-Prot Saccharide-COOH+EDAC+NH2----SH----->saccharide----SH+maleimide-Prot (modification of amino groups)---->conjugate Saccharide-Aldehyde+NH2 NH2---->saccharide---NH2+EDAC+COOH-Prot---->conjugate Note: instead of EDAC above, any suitable carbodiimide may be used.

In summary, the types of protein carrier chemical group that may be generally used for coupling with a saccharide are amino groups (for instance on lysine residues), COOH groups (for instance on aspartic and glutamic acid residues) and SH groups (if accessible) (for instance on cysteine residues).

In an embodiment, the Hib saccharide, where present, is conjugated to the carrier protein using CNBr, or CDAP, or a combination of CDAP and carbodiimide chemistry (such as EDAC), or a combination of CNBr and carbodiimide chemistry (such as EDAC). Optionally Hib is conjugated using CNBr and carbodiimide chemistry, optionally EDAC. For example, CNBr is used to join the saccharide and linker and then carbodiimide chemistry is used to join linker to the protein carrier.

In an embodiment, at least one of the *N. meningitidis* capsular saccharides (or saccharide in general) is directly conjugated to a carrier protein; optionally Men W and/or MenY and/or MenC saccharide(s) is directly conjugated to a carrier protein. For example MenW; MenY; MenC; MenW and MenY; MenW and MenC; MenY and MenC; or MenW, MenY and MenC are directly linked to the carrier protein. Optionally, at least one of the *N. meningitidis* capsular saccharides is directly conjugated by CDAP. For example MenW; MenY; MenC; MenW and MenY; MenW and MenC; MenY and MenC; or MenW, MenY and MenC are directly linked to the carrier protein by CDAP (see WO 95/08348 and WO 96/29094). In an embodiment, all *N. meningitidis* capsular saccharides are conjugated to tetanus toxoid.

In an embodiment, the ratio of Men W and/or Y saccharide to carrier protein is between 1:0.5 and 1:2 (w/w) and/or the ratio of MenC saccharide to carrier protein is between 1:0.5 and 1:4 or 1:0.5 and 1:1.5 (w/w), especially where these saccharides are directly linked to the protein, optionally using CDAP.

In an embodiment, at least one of the *N. meningitidis* capsular saccharide(s) (or saccharide in general) is conjugated to the carrier protein via a linker, for instance a bifunctional linker. The linker is optionally heterobifunctional or homobifunctional, having for example a reactive amine group and a reactive carboxylic acid group, 2 reactive amine groups or 2 reactive carboxylic acid groups. The linker has for example between 4 and 20, 4 and 12, 5 and 10 carbon atoms. A possible linker is ADH.

In an embodiment, MenA; MenC; or MenA and MenC is conjugated to a carrier protein (for example tetanus toxoid) via a linker.

In an embodiment, at least one *N. meningitidis* saccharide is conjugated to a carrier protein via a linker using CDAP and EDAC. For example, MenA; MenC; or MenA and MenC are conjugated to a protein via a linker (for example those with two hydrazino groups at its ends such as ADH) using CDAP and EDAC as described above. For example, CDAP is used to conjugate the saccharide to a linker and EDAC is used to conjugate the linker to a protein. Optionally the conjugation via a linker results in a ratio of saccharide to carrier protein of of between 1:0.5 and 1:6; 1:1 and 1:5 or 1:2 and 1:4, for MenA; MenC; or MenA and MenC.

In an embodiment, the MenA capsular saccharide, where present is at least partially O-acetylated such that at least 50%, 60%, 70%, 80%, 90%, 95% or 98% of the repeat units are O-acetylated at at least one position. O-acetylation is for example present at least at the O-3 position of at least 50%, 60%, 70%, 80%, 90%, 95% or 98% of the repeat units.

In an embodiment, the MenC capsular saccharide, where present is is at least partially O-acetylated such that at least 30%, 40%, 50%, 60%, 70%, 80%, 90%, 95% or 98% of ($\alpha 2 \rightarrow 9$)-linked NeuNAc repeat units are O-acetylated at at least one or two positions. O-acetylation is for example present at the O-7 and/or O-8 position of at least 30%. 40%, 50%, 60%, 70%, 80%, 90%, 95% or 98% of the repeat units.

In an embodiment, the MenW capsular saccharide, where present is is at least partially O-acetylated such that at least 30%, 40%, 50%, 60%, 70%, 80%, 90%, 95% or 98% of the repeat units are O-acetylated at at least one or two positions. 0-acetylation is for example present at the O-7 and/or O-9 position of at least 30%. 40%, 50%, 60%, 70%, 80%, 90%, 95% or 98% of the repeat units.

In an embodiment, the MenY capsular saccharide, where present is at least partially O-acetylated such that at least 20%, 30%, 40%, 50%, 60%, 70%, 80%, 90%, 95% or 98% of the repeat units are O-acetylated at at least one or two positions. O-acetylation is present at the 7 and/or 9 position of at least 20%, 30%, 40%, 50%, 60%, 70%, 80%, 90%, 95% or 98% of the repeat units.

The percentage of O-acetylation refers to the percentage of the repeat units containing O-acetylation. This may be measured in the saccharide prior to conjugate and/or after conjugation.

In one embodiment of the invention the immunogenic composition, saccharide present, or each *N. meningitidis* capsular saccharide present, is conjugated to TT. In a further embodiment each *N. meningitidis* capsular saccharide is separately conjugated to a separate carrier protein. In a further embodiment each *N. meningitidis* capsular saccharide conjugate has a saccharide:carrier ratio of 1:5-5:1 or 1:1-1:4 (w/w). In a further embodiment at least one, two or three *N. meningitidis* capsular saccharide conjugate(s) is directly conjugated to a carrier protein. In a further embodiment Men W and/or MenY, MenW and/or MenC, MenY and/or MenC, or MenW and MenC and MenY are directly conjugated to a carrier protein. In a further embodiment at least one, two or three *N. meningitidis* saccharide conjugate(s) is directly conjugated by CDAP chemistry. In a further embodiment the ratio of Men W and/or Y saccharide to carrier protein is between 1:0.5 and 1:2 (w/w). In a further embodiment the ratio of MenC saccharide to carrier protein is between 1:0.5 and 1:2 (w/w). In a further embodiment at least one, two or three *N. meningitidis* capsular saccharide(s) are conjugated to the carrier protein via a linker (which may be bifunctional such as having two reactive amino groups (such as ADH) or two reactive carboxyl groups, or a reactive amino group at one end and a reactive carboxyl group at the other). The linker can have between 4 and 12 carbon atoms. In a further embodiment the or each *N. meningitidis* capsular saccharide(s) conjugated via a linker are conjugated to the linker with CDAP chemistry. In a further embodiment the carrier protein is conjugated to the linker using carbodiimide chemistry, for example using EDAC. In a further embodiment the or each *N. meningitidis* capsular saccharide is conjugated to the linker before the carrier protein is conjugated to the linker. In a further embodiment MenA is conjugated to a carrier protein via a linker (the ratio of MenA saccharide to carrier protein may be between 1:2 and 1:5 (w/w)). In a further embodiment MenC is conjugated to a carrier protein via a linker (the ratio of MenC saccharide to carrier protein may be between 1:2 and 1:5 (w/w)).

The inventors have also noted that the focus of the art has been to use oligosaccharides for ease of conjugate production. The inventors have found that by using native or slightly sized polysaccharide conjugates, one or more of the following advantages may be realised: 1) a conjugate having high immunogenicity which is filterable through a 0.2 micron filter; 2) immune memory may be enhanced (as in example three); 3) the alteration of the ratio of polysaccharide to protein in the conjugate such that the ratio of polysaccharide to protein (w/w) in the conjugate may be increased (this can result in a reduction of the carrier suppression effect); 4) immunogenic conjugates prone to hydrolysis (such as MenA conjugates) may be stabilised by the use of larger polysaccharides for conjugation. The use of larger polysaccharides can result in more cross-linking with the conjugate carrier and may lessen the liberation of free saccharide from the conjugate. The conjugate vaccines described in the prior art tend to depolymerise the polysaccharides prior to conjugation in order to improve conjugation. The present inventors have found that meningococcal (or saccharide) conjugate vaccines retaining a larger size of saccharide can provide a good immune response against meningococcal disease.

The immunogenic composition of the invention may thus comprise one or more saccharide conjugates wherein the average size of each saccharide before conjugation is above 50 kDa, 75 kDa, 100 kDa, 110 kDa, 120 kDa or 130 kDa. In one embodiment the conjugate post conjugation should be readily filterable through a 0.2 micron filter such that a yield of more than 50, 60, 70, 80, 90 or 95% is obtained post filtration compared with the pre filtration sample.

In particular, the immunogenic composition of the invention comprises *N. meningitidis* capsular saccharides from at least one, two, three or four of serogroups A, C, W and Y conjugated to a carrier protein, wherein the average size (weight-average molecular weight; Mw) of at least one, two, three or four or each *N. meningitidis* saccharide is above 50 kDa, 60 kDa, 75 kDa, 100 kDa, 110 kDa, 120 kDa or 130 kDa.

The immunogenic composition may comprise *N. meningitidis* capsular saccharides from at least one, two, three or four of serogroups A, C, W and Y conjugated to a carrier protein, wherein at least one, two, three or four or each *N. meningitidis* saccharide is either a native saccharide or is sized by a factor up to ×2, ×3, ×4, ×5, ×6, ×7, ×8, ×9 or ×10 relative to the weight average molecular weight of the native polysaccharide.

For the purposes of the invention, "native polysaccharide" refers to a saccharide that has not been subjected to a process, the purpose of which is to reduce the size of the saccharide. A polysaccharide can become slightly reduced in size during normal purification procedures. Such a saccharide is still native. Only if the polysaccharide has been subjected to sizing techniques would the polysaccharide not be considered native.

For the purposes of the invention, "sized by a factor up to ×2" means that the saccharide is subject to a process intended to reduce the size of the saccharide but to retain a size more than half the size of the native polysaccharide. ×3, ×4 etc. are to be interpreted in the same way i.e. the saccharide is subject to a process intended to reduce the size of the polysaccharide but to retain a size more than a third, a quarter etc. the size of the native polysaccharide.

In an aspect of the invention, the immunogenic composition comprises *N. meningitidis* capsular saccharides from at least one, two, three or four of serogroups A, C, W and Y conjugated to a carrier protein, wherein at least one, two, three or four or each *N. meningitidis* saccharide is native polysaccharide.

In an aspect of the invention, the immunogenic composition comprises *N. meningitidis* capsular saccharides from at least one, two, three or four of serogroups A, C, W and Y conjugated to a carrier protein, wherein at least one, two, three or four or each *N. meningitidis* saccharide is sized by a factor up to ×1.5, ×2, ×3, ×4, ×5, ×6, ×7, ×8, ×9 or ×10.

The immunogenic compositions of the invention optionally comprise conjugates of: *N. meningitidis* serogroup C capsular saccharide (MenC), serogroup A capsular saccharide (MenA), serogroup W135 capsular saccharide (MenW), serogroup Y capsular saccharide (MenY), serogroup C and Y capsular saccharides (MenCY), serogroup C and A capsular saccharides (MenAC), serogroup C and W capsular saccharides (MenCW), serogroup A and Y capsular saccharide (MenAY), serogroup A and W capsular saccharides (MenAW), serogroup W and Y capsular saccharides (MenWY), serogroup A, C and W capsular saccharide (MenACW), serogroup A, C and Y capsular saccharides (MenACY); serogroup A, W135 and Y capsular saccharides (MenAWY), serogroup C, W135 and Y capsular saccharides (MenCWY); or serogroup A, C, W135 and Y capsular saccharides (MenACWY). This is the definition of "one, two, three or four", or "at least one of" of serogroups A, C, W and Y, or of each *N. meningitidis* saccharide where mentioned herein.

In an embodiment, the average size of at least one, two, three, four or each *N. meningitidis* saccharide is between 50 KDa and 1500 kDa, 50 kDa and 500 kDa, 50 kDa and 300 KDa, 101 kDa and 1500 kDa, 101 kDa and 500 kDa, 101 kDa and 300 kDa as determined by MALLS.

In an embodiment, the MenA saccharide, where present, has a molecular weight of 50-500 kDa, 50-100 kDa, 100-500 kDa, 55-90 KDa, 60-70 kDa or 70-80 kDa or 60-80 kDa.

In an embodiment, the MenC saccharide, where present, has a molecular weight of 100-200 kDa, 50-100 kDa, 100-150 kDa, 101-130 kDa, 150-210 kDa or 180-210 kDa.

In an embodiment the MenY saccharide, where present, has a molecular weight of 60-190 kDa, 70-180 kDa, 80-170 kDa, 90-160 kDa, 100-150 kDa or 110-140 kDa, 50-100 kDa, 100-140 kDa, 140-170 kDa or 150-160 kDa.

In an embodiment the MenW saccharide, where present, has a molecular weight of 60-190 kDa, 70-180 kDa, 80-170 kDa, 90-160 kDa, 100-150 kDa, 110-140 kDa, 50-100 kDa or 120-140 kDa.

The molecular weight or average molecular weight of a saccharide herein refers to the weight-average molecular weight (Mw) of the saccharide measured prior to conjugation and is measured by MALLS.

The MALLS technique is well known in the art and is typically carried out as described in example 2. For MALLS analysis of meningococcal saccharides, two columns (TSKG6000 and 5000PWxl) may be used in combination and the saccharides are eluted in water. Saccharides are detected using a light scattering detector (for instance Wyatt Dawn DSP equipped with a 10 mW argon laser at 488 nm) and an inferometric refractometer (for instance Wyatt Otilab DSP equipped with a P100 cell and a red filter at 498 nm).

In an embodiment the N. meningitidis saccharides are native polysaccharides or native polysaccharides which have reduced in size during a normal extraction process.

In an embodiment, the N. meningitidis saccharides are sized by mechanical cleavage, for instance by microfluidisation or sonication. Microfluidisation and sonication have the advantage of decreasing the size of the larger native polysaccharides sufficiently to provide a filterable conjugate (fro example through a 0.2 micron filter). Sizing is by a factor of no more than ×20, ×10, ×8, ×6, ×5, ×4, ×3, ×2 or ×1.5.

In an embodiment, the immunogenic composition comprises N. meningitidis conjugates that are made from a mixture of native polysaccharides and saccharides that are sized by a factor of no more than ×20. For example, saccharides from MenC and/or MenA are native. For example, saccharides from MenY and/or MenW are sized by a factor of no more than ×20, ×10, ×8, ×6, ×5, ×4, ×3 or ×2. For example, an immunogenic composition contains a conjugate made from MenY and/or MenW and/or MenC and/or MenA which is sized by a factor of no more then ×10 and/or is microfluidised. For example, an immunogenic composition contains a conjugate made from native MenA and/or MenC and/or MenW and/or MenY. For example, an immunogenic composition comprises a conjugate made from native MenC. For example, an immunogenic composition comprises a conjugate made from native MenC and MenA which is sized by a factor of no more then ×10 and/or is microfluidised. For example, an immunogenic composition comprises a conjugate made from native MenC and MenY which is sized by a factor of no more then ×10 and/or is microfluidised.

In an embodiment, the polydispersity of the saccharide is 1-1.5, 1-1.3, 1-1.2, 1-1.1 or 1-1.05 and after conjugation to a carrier protein, the polydispersity of the conjugate is 1.0-2.5, 1.0-2.0. 1.0-1.5, 1.0-1.2, 1.5-2.5, 1.7-2.2 or 1.5-2.0. All polydispersity measurements are by MALLS.

Saccharides are optionally sized up to 1.5, 2, 4, 6, 8, 10, 12, 14, 16, 18 or 20 times from the size of the polysaccharide isolated from bacteria.

In one embodiment each N. meningitidis saccharide is either a native polysaccharide or is sized by a factor of no more than ×10. In a further embodiment each N. meningitidis capsular saccharide is a native polysaccharide. In a further embodiment at least one, two, three or four N. meningitidis capsular saccharide(s) is sized by microfluidization. In a further embodiment each N. meningitidis capsular saccharide is sized by a factor of no more than ×10. In a further embodiment the N. meningitidis conjugates are made from a mixture of native polysaccharides and saccharides that are sized by a factor of no more than ×10. In a further embodiment the capsular saccharide from serogroup Y is sized by a factor of no more than ×10. In a further embodiment capsular saccharides from serogroups A and C are native polysaccharides and saccharides from serogroups W135 and Y are sized by a factor of no more than ×10. In a further embodiment the average size of each N. meningitidis capular saccharide is between 50 kDa and 300 KDa or 50 kDa and 200 kDa. In a further embodiment the immunogenic composition comprises a MenA capsular saccharide having an average size of above 50 kDa, 75 kDa, 100 kDa or an average size of between 50-100 kDa or 55-90 KDa or 60-80 kDa. In a further embodiment the immunogenic composition comprises a MenC capsular saccharide having an average size of above 50 kDa, 75 kDa, 100 kDa or between 100-200 kDa, 100-150 kDa, 80-120 kDa, 90-110 kDa, 150-200 kDa, 120-240 kDa, 140-220 kDa, 160-200 kDa or 190-200 kDa. In a further embodiment the immunogenic composition comprises a MenY capsular saccharide, having an average size of above 50 kDa, 75 kDa, 100 kDa or between 60-190 kDa or 70-180 kDa or 80-170 kDa or 90-160 kDa or 100-150 kDa, 110-145 kDa or 120-140 kDa. In a further embodiment the immunogenic composition comprises a MenW capsular saccharide having an average size of above 50 kDa, 75 kDa, 100 kDa or between 60-190 kDa or 70-180 kDa or 80-170 kDa or 90-160 kDa or 100-150 kDa, 140-180 kDa, 150-170 kDa or 110-140 kDa.

The immunogenic composition of the invention may comprise a H. influenzae b capsular saccharide (Hib) conjugated to a carrier protein. This may be conjugated to a carrier protein selected from the group consisting of TT, DT, CRM197, fragment C of TT and protein D, for instance TT. The Hib saccharide may be conjugated to the same carrier protein as for at least one, two, three or all of the N. meningitidis capsular saccharide conjugates, for instance TT. The ratio of Hib to carrier protein in the Hib capsular saccharide conjugate may be between 1:5 and 5:1 (w/w), for instance between 1:1 and 1:4, 1:2 and 1:3.5 or around 1:3 (w/w). The Hib capsular saccharide may be conjugated to the carrier protein via a linker (see above). The linker may bifunctional (with two reactive amino groups, such as ADH, or two reactive carboxylic acid groups, or a reactive amino group at one end and a reactive carboxylic acid group at the other end). It may have between 4 and 12 carbon atoms. Hib saccharide may be conjugated to the carrier protein or linker using CNBr or CDAP. The carrier protein may be conjugated to the Hib saccharide via the linker using a method comprising carbodiimide chemistry, for example EDAC chemistry (thus using the carboxyl chemical group on the carrier). The dose of the Hib saccharide conjugate may be between 0.1 and 9 µg, 1 and 5 µg or 2 and 3 µg of saccharide.

In a further embodiment, the immunogenic composition of the invention comprises a Hib saccharide conjugate and at least two N. meningitidis saccharide conjugates wherein the Hib conjugate is present in a lower saccharide dose than the mean saccharide dose of the at least two N. meningitidis saccharide conjugates. Alternatively, the Hib conjugate is present in a lower saccharide dose than the saccharide dose of each of the at least two N. meningitidis saccharide conjugates. For example, the dose of the Hib conjugate may be at least 10%, 20%, 30%, 40%, 50%, 60%, 70% or 80% lower than the mean or lowest saccharide dose of the at least two further N. meningitidis saccharide conjugates.

The mean dose is determined by adding the doses of all the further saccharides and dividing by the number of further saccharides. Further saccharides are all the saccharides within the immunogenic composition apart from Hib and can include N. meningitidis capsular saccharides. The "dose" is in the amount of immunogenic composition or vaccine that is administered to a human.

A Hib saccharide is the polyribosyl phosphate (PRP) capsular polysaccharide of *Haemophilus influenzae* type b or an oligosaccharide derived therefrom.

At least two further bacterial saccharide conjugates is to be taken to mean two further bacterial saccharide conjugates in addition to a Hib conjugate. The two further bacterial conjugates may include *N. meningitidis* capular saccharide conjugates.

The immunogenic compositions of the invention may comprise further saccharide conjugates derived from one or more of *Neisseria meningitidis, Streptococcus pneumoniae*, Group A Streptococci, Group B Streptococci, *S. typhi, Staphylococcus aureus* or *Staphylococcus epidermidis*. In an embodiment, the immunogenic composition comprises capsular saccharides derived from one or more of serogroups A, C, W135 and Y of *Neisseria meningitidis*. A further embodiment comprises capsular saccharides derived from *Streptococcus pneumoniae*. The pneumococcal capsular saccharide antigens are optionally selected from serotypes 1, 2, 3, 4, 5, 6A, 6B, 7F, 8, 9N, 9V, 10A, 11A, 12F, 14, 15B, 17F, 18C, 19A, 19F, 20, 22F, 23F and 33F (optionally from serotypes 1, 3, 4, 5, 6B, 7F, 9V, 14, 18C, 19F and 23F). A further embodiment comprises the Type 5, Type 8 or 336 capsular saccharides of *Staphylococcus aureus*. A further embodiment comprises the Type I, Type II or Type III capsular saccharides of *Staphylococcus epidermidis*. A further embodiment comprises the Vi saccharide from *S. typhi*. A further embodiment comprises the Type Ia, Type Ic, Type II, Type III or Type V capsular saccharides of Group B *strepcooocus*. A further embodiment comprises the capsular saccharides of Group A *streptococcus*, optionally further comprising at least one M protein and optionally multiple types of M protein.

The immunogenic compositions of the invention may also comprise a DTPa or DTPw vaccine (for instance one containing DT, TT, and either a whole cell pertussis (Pw) vaccine or an acellular pertussis (Pa) vaccine (comprising for instance pertussis toxoid, FHA, pertactin, and, optionally agglutinogins 2 and 3). Such combinations may also comprise a vaccine against hepatitis B (for instance it may comprise hepatitis B surface antigen [HepB], optionally adsorbed onto aluminium phosphate). In one embodiment the immunogenic composition of the invention comprises a DTPwHepBHibMenAC vaccine where the HibMenAC component is as described above.

Immunogenic compositions of the invention optionally comprise additional viral antigens conferring protection against disease caused by measles and/or mumps and/or rubella and/or varicella. For example, immunogenic composition of the invention contains antigens from measles, mumps and rubella (MMR) or measles, mumps, rubella and varicella (MMRV). In an embodiment, these viral antigens are optionally present in the same container as the meningococcal and/or Hib saccharide conjugate(s). In an embodiment, these viral antigens are lyophilised.

In an embodiment, the immunogenic composition of the invention further comprises an antigen from *N. meningitidis* serogroup B. The antigen is optionally a capsular polysaccharide from *N. meningitidis* serogroup B (MenB) or a sized polysaccharide or oligosaccharide derived therefrom, which may be conjugated to a protein carrier. The antigen is optionally an outer membrane vesicle preparation from *N. meningitidis* serogroup B as described in EP301992, WO 01/09350, WO 04/14417, WO 04/14418 and WO 04/14419.

In general, the immunogenic composition of the invention may comprise a dose of each saccharide conjugate between 0.1 and 20 µg, 2 and 10 µg, 2 and 6 µg or 4 and 7 µg of saccharide.

In an embodiment, the immunogenic composition of the invention contains each *N. meningitidis* capsular saccharide at a dose of between 0.1-20 µg; 1-10 µg; 2-10 µg, 2.5-5 µg, around or exactly 5 µg; or around or exactly 2.5 µg. In an embodiment, the immunogenic composition of the invention comprises MenA, MenC, MenW and MenY (optionally conjugated to tetanus toxoid) in doses of 2.5, 2.5, 2.5 and 2.5 µg respectively, 5, 5, 5 and 5 µg respectively or 5, 5, 2, 5 and 2.5 µg respectively.

In an embodiment, the immunogenic composition of the invention for example contains the Hib saccharide conjugate at a saccharide dose between 0.1 and 9 µg; 1 and 5 µg or 2 and 3 µg or around or exactly 2.5 µg. In a further embodiment the immunogenic composition of the invention for example contains the Hib saccharide conjugate at a saccharide dose between 0.1 and 9 µg; 1 and 5 µg or 2 and 3 µg or around or exactly 2.5 µg and each of the *N. meningitidis* polysaccharide conjugates at a saccharide dose of between 2 and 20 µg, 3 and 10 µg, or between 4 and 7 µg or around or exactly 5 µg.

"Around" or "approximately" are defined as within 10% more or less of the given figure for the purposes of the invention.

In an embodiment, the immunogenic composition of the invention may contain a saccharide dose of the Hib saccharide conjugate which is for example less than 90%, 80%, 75%, 70%, 60%, 50%, 40%, 30%, 20% or 10% of the mean saccharide dose of at least two, three, four or each of the *N. meningitidis* saccharide conjugates. The saccharide dose of the Hib saccharide is for example between 20% and 60%, 30% and 60%, 40% and 60% or around or exactly 50% of the mean saccharide dose of at least two, three, four or each of the *N. meningitidis* saccharide conjugates.

In an embodiment, the immunogenic composition of the invention contains a saccharide dose of the Hib saccharide conjugate which is for example less than 90%, 80%, 75%, 70%, 60%, 50%, 40%, 30%, 20% or 10% of the lowest saccharide dose of the at least two, three, four or each of the *N. meningitidis* saccharide conjugates. The saccharide dose of the Hib saccharide is for example between 20% and 60%, 30% and 60%, 40% and 60% or around or exactly 50% of the lowest saccharide dose of the at least two, three, four or each of the *N. meningitidis* saccharide conjugates.

In an embodiment of the invention, the saccharide dose of each of the at least two, three, four or each of the *N. meningitidis* saccharide conjugates is optionally the same, or approximately the same.

Examples of immunogenic compositions of the invention are compositions consisting of or comprising:

Hib conjugate and MenA conjugate and MenC conjugate, optionally at saccharide dose ratios of 1:2:2, 1:2:1, 1:4:2, 1:6:3, 1:3:3, 1:4:4, 1:5:5, 1:6:6 (w/w). Optionally, the saccharide dose of MenA is greater than the saccharide dose of MenC.

Hib conjugate and MenC conjugate and MenY conjugate, optionally at saccharide dose ratios of 1:2:2, 1:2:1, 1:4:2, 1:4:1, 1:8:4, 1:6:3, 1:3:3, 1:4:4, 1:5:5, 1:6:6 (w/w).

Optionally, the saccharide dose of MenC is greater than the saccharide dose of MenY.

Hib conjugate and MenC conjugate and MenW conjugate, optionally at saccharide dose ratios of 1:2:2, 1:2:1, 1:4:2, 1:4:1, 1:8:4, 1:6:3, 1:3:3, 1:4:4, 1:5:5, 1:6:6 (w/w). Optionally the saccharide dose of MenC is greater than the saccharide dose of MenW.

Hib conjugate and MenA conjugate and MenW conjugate, optionally at saccharide dose ratios of 1:2:2, 1:2:1, 1:4:2, 1:4:1, 1:8:4, 1:6:3, 1:3:3, 1:4:4, 1:5:5, 1:6:6 (w/w). Optionally, the saccharide dose of MenA is greater than the saccharide dose of MenW.

Hib conjugate and MenA conjugate and MenY conjugate, optionally at saccharide dose ratios of 1:2:2, 1:2:1, 1:4:2, 1:4:1, 1:8:4, 1:6:3, 1:3:3, 1:4:4, 1:5:5, 1:6:6 (w/w). Optionally the saccharide dose of MenA is greater than the saccharide dose of MenY.

Hib conjugate and MenW conjugate and MenY conjugate, optionally at saccharide dose ratios of 1:2:2, 1:2:1, 1:1:2, 1:4:2, 1:2:4, 1:4:1, 1:1:4, 1:3:6, 1:1:3, 1:6:3, 1:3:3, 1:4:4, 1:5:5, 1:6:6 (w/w). Optionally the saccharide dose of MenY is greater than the saccharide dose of MenW.

MenA, MenC, MenW and MenY at saccharide dose ratios of 1:1:1:1 or 2:1:1:1 or 1:2:1:1 or 2:2:1:1 or 1:3:1:1 or 1:4:1:1 (w/w).

A further aspect of the invention is a vaccine comprising the immunogenic composition of the invention and a pharmaceutically acceptable excipient.

In an embodiment, the immunogenic composition of the invention is adjusted to or buffered at, or adjusted to between pH 7.0 and 8.0, pH 7.2 and 7.6 or around or exactly pH 7.4.

The immunogenic composition or vaccines of the invention are optionally lyophilised in the presence of a stabilising agent for example a polyol such as sucrose or trehalose.

Optionally, the immunogenic composition or vaccine of the invention contains an amount of an adjuvant sufficient to enhance the immune response to the immunogen. Suitable adjuvants include, but are not limited to, aluminium salts (aluminium phosphate or aluminium hydroxide), squalene mixtures (SAF-1), muramyl peptide, saponin derivatives, *mycobacterium* cell wall preparations, monophosphoryl lipid A, mycolic acid derivatives, non-ionic block copolymer surfactants, Quil A, cholera toxin B subunit, polyphosphazene and derivatives, and immunostimulating complexes (ISCOMs) such as those described by Takahashi et al. (1990) Nature 344:873-875.

For the *N. meningitidis* or HibMen combinations discussed above, it may be advantageous not to use any aluminium salt adjuvant or any adjuvant at all.

As with all immunogenic compositions or vaccines, the immunologically effective amounts of the immunogens must be determined empirically. Factors to be considered include the immunogenicity, whether or not the immunogen will be complexed with or covalently attached to an adjuvant or carrier protein or other carrier, route of administrations and the number of immunising dosages to be administered.

The active agent can be present in varying concentrations in the pharmaceutical composition or vaccine of the invention. Typically, the minimum concentration of the substance is an amount necessary to achieve its intended use, while the maximum concentration is the maximum amount that will remain in solution or homogeneously suspended within the initial mixture. For instance, the minimum amount of a therapeutic agent is optionally one which will provide a single therapeutically effective dosage. For bioactive substances, the minimum concentration is an amount necessary for bioactivity upon reconstitution and the maximum concentration is at the point at which a homogeneous suspension cannot be maintained. In the case of single-dosed units, the amount is that of a single therapeutic application. Generally, it is expected that each dose will comprise 1-100 µg of protein antigen, optionally 5-50 µg or 5-25 µg. For example, doses of bacterial saccharides are 10-20 µg, 5-10 µg, 2.5-5 µg or 1-2.5 µg of saccharide in the conjugate.

The vaccine preparations of the present invention may be used to protect or treat a mammal (for example a human patient) susceptible to infection, by means of administering said vaccine via systemic or mucosal route. A human patient is optionally an infant (under 12 months), a toddler (12-24, 12-16 or 12-14 months), a child (2-10, 3-8 or 3-5 years) an adolescent (12-21, 14-20 or 15-19 years) or an adult. These administrations may include injection via the intramuscular, intraperitoneal, intradermal or subcutaneous routes; or via mucosal administration to the oral/alimentary, respiratory, genitourinary tracts. Intranasal administration of vaccines for the treatment of pneumonia or otitis media is preferred (as nasopharyngeal carriage of pneumococci can be more effectively prevented, thus attenuating infection at its earliest stage). Although the vaccine of the invention may be administered as a single dose, components thereof may also be co-administered together at the same time or at different times (for instance if saccharides are present in a vaccine these could be administered separately at the same time or 1-2 weeks after the administration of a bacterial protein vaccine for optimal coordination of the immune responses with respect to each other). In addition to a single route of administration, 2 different routes of administration may be used. For example, viral antigens may be administered ID (intradermal), whilst bacterial proteins may be administered IM (intramuscular) or IN (intranasal). If saccharides are present, they may be administered IM (or ID) and bacterial proteins may be administered IN (or ID). In addition, the vaccines of the invention may be administered IM for priming doses and IN for booster doses.

Vaccine preparation is generally described in Vaccine Design ("The subunit and adjuvant approach" (eds Powell M. F. & Newman M. J.) (1995) Plenum Press New York). Encapsulation within liposomes is described by Fullerton, U.S. Pat. No. 4,235,877.

A further aspect of the invention is a vaccine kit for concomitant or sequential administration comprising two multi-valent immunogenic compositions for conferring protection in a host against disease caused by *Bordetella pertussis, Clostridium tetani, Corynebacterium diphtheriae* and *Neisseria meningitidis* and optionally *Haemophilus influenzae*. For example, the kit optionally comprises a first container comprising one or more of:

tetanus toxoid (TT),
diphtheria toxoid (DT), and
whole cell or acellular pertussis components
and a second container comprising:
an immunogenic composition of the invention as described above (for instance those comprising Men or HibMen saccharide conjugate combinations).

A further aspect of the invention is a vaccine kit for concomitant or sequential administration comprising two multi-valent immunogenic compositions for conferring protection in a host against disease caused by *Streptococcus pneumoniae* and *Neisseria meningitidis* and optionally *Haemophilus influenzae*. For example, the kit optionally comprises a first container comprising:

one or more conjugates of a carrier protein and a capsular saccharide from *Streptococcus pneumoniae* [where the capsular saccharide is optionally from a pneumococcal serotype selected from the group consisting of 1, 2, 3, 4, 5, 6A, 6B, 7F, 8, 9N, 9V, 10A, 11A, 12F, 14, 15B, 17F, 18C, 19A, 19F, 20, 22F, 23F and 33F].

and a second container comprising:
an immunogenic composition of the invention as described above (for instance those comprising Men or HibMen saccharide conjugate combinations).

Examples of the Hib conjugate and the *N. meningitidis* polysaccharide conjugates are as described above.

Typically the *Streptococcus pneumoniae* vaccine in the vaccine kit of the present invention (or in any of the immunogenic compositions of the invention described above) will comprise saccharide antigens (optionally conjugated), wherein the saccharides are derived from at least four serotypes of pneumococcus chosen from the group consisting of 1, 2, 3, 4, 5, 6A, 6B, 7F, 8, 9N, 9V, 10A, 11A, 12F, 14, 15B, 17F, 18C, 19A, 19F, 20, 22F, 23F and 33F. Optionally, the four serotypes include 6B, 14, 19F and 23F. Optionally, at least 7 serotypes are included in the composition, for example those derived from serotypes 4, 6B, 9V, 14, 18C, 19F, and 23F. Optionally more than 7 serotypes are included in the composition, for instance at least 10, 11, 12, 13 or 14 serotypes. For example the composition in one embodiment includes 10 or 11 capsular saccharides derived from serotypes 1, 4, 5, 6B, 7F, 9V, 14, 18C, 19F and 23F, and optionally 3 (all optionally conjugated). In an embodiment of the invention at least 13 saccharide antigens (optionally conjugated) are included, although further saccharide antigens, for example 23 valent (such as serotypes 1, 2, 3, 4, 5, 6B, 7F, 8, 9N, 9V, 10A, 11A, 12F, 14, 15B, 17F, 18C, 19A, 19F, 20, 22F, 23F and 33F), are also contemplated by the invention.

The pneumococcal saccharides are independently conjugated to any known carrier protein, for example CRM197, tetanus toxoid, diphtheria toxoid, protein D or any other carrier proteins as mentioned above.

Optionally, the vaccine kits of the invention comprise a third component. For example, the kit optionally comprises a first container comprising one or more of:
tetanus toxoid (TT),
diphtheria toxoid (DT), and
whole cell or acellular pertussis components
and a second container comprising:
one or more conjugates of a carrier protein and a capsular saccharide from *Streptococcus pneumoniae* [where the capsular saccharide is optionally from a pneumococcal serotype selected from the group consisting of 1, 2, 3, 4, 5, 6A, 6B, 7F, 8, 9N, 9V, 10A, 11A, 12F, 14, 15B, 17F, 18C, 19A, 19F, 20, 22F, 23F and 33F].
and a third container comprising:
an immunogenic composition of the invention as described above (for instance those comprising Men or HibMen saccharide conjugate combinations).

A further aspect of the invention is a process for making the immunogenic composition or vaccine of the invention, comprising the step of mixing the saccharides of the invention, for instance mixing *N. meningitidis* capsular saccharides from at least one, two, three or all four of serogroups A, C, W and Y conjugated to a carrier protein with a pharmaceutically acceptable excipient.

A further aspect of the invention is a method of immunising a human host against disease caused by bacteria, for example *N. meningitidis* and optionally *Haemophilus influenzae* infection comprising administering to the host an immunoprotective dose of the immunogenic composition or vaccine or kit of the invention, optionally using a single dose.

An independent aspect of the invention is a method of immunising a human host with an immunogenic composition comprising at least 2 different *N. meningitidis* capsular saccharide conjugates selected from the group consisting of serogroup A, C, W and Y (optionally MenA, C, W and Y) wherein a single dose administration (optionally to teenagers, adults or children) results in a blood test taken one month after administration giving over 50%, 60%, 70%, 80%, 90% or 95% responders in an SBA assay measuring levels of response against MenA, MenC, MenW and/or MenY. Optionally the SBA assay is as described in Example 9 with responder assessed as described in Example 9.

A further independent aspect of the invention is an immunogenic composition comprising MenA, MenC, MenW and/or MenY conjugates which is capable of eliciting an immune response after a single dose such that over 50%, 60%, 70%, 80%, 90% or 95% of human subjects (children, teenagers or adults) inoculated are classified as responders in an SBA assay on blood extracted a month after inoculation (optionally using the criteria described in example 9).

Such an immunogenic composition optionally has the further structural characteristics described herein.

A further aspect of the invention is an immunogenic composition of the invention for use in the treatment or prevention of disease caused by bacteria, for example *N. meningitidis* and optionally *Haemophilus influenzae* infection.

A further aspect of the invention is use of the immunogenic composition or vaccine or kit of the invention in the manufacture of a medicament for the treatment or prevention of diseases caused by bacteria for example *N. meningitidis* and optionally *Haemophilus influenzae* infection.

The terms "comprising", "comprise" and "comprises" herein are intended by the inventors to be optionally substitutable with the terms "consisting of", "consist of" and "consists of", respectively, in every instance.

All references or patent applications cited within this patent specification are incorporated by reference herein.

The invention is illustrated in the accompanying examples. The examples below are carried out using standard techniques, which are well known and routine to those of skill in the art, except where otherwise described in detail. The examples are illustrative, but do not limit the invention.

EXAMPLES

Example 1—Preparation of Polysaccharide Conjugates

The covalent binding of *Haemophilus influenzae* (Hib) PRP polysaccharide to TT was carried out by a coupling chemistry developed by Chu et al. (Infection and Immunity 1983, 40 (1); 245-256). Hib PRP polysaccharide was activated by adding CNBr and incubating at pH10.5 for 6 minutes. The pH was lowered to pH8.75 and adipic acid dihydrazide (ADH) was added and incubation continued for a further 90 minutes. The activated PRP was coupled to purified tetanus toxoid via carbodiimide condensation using 1-ethyl-3-(3-dimethyl-aminopropyl)carbodiimide (EDAC). EDAC was added to the activated PRP to reach a final ratio of 0.6 mg EDAC/mg activated PRP. The pH was adjusted to 5.0 and purified tetanus toxoid was added to reach 2 mg TT/mg activated PRP. The resulting solution was left for three days with mild stirring. After filtration through a 0.45 μm membrane, the conjugate was purified on a Sephacryl® S500HR (Pharmacia, Sweden) column equilibrated in 0.2M NaCl.

MenC-TT conjugates were produced using native polysaccharides (of over 150 kDa as measured by MALLS) or were slightly microfluidised. MenA-TT conjugates were produced using either native polysaccharide or slightly microfluidised polysaccharide of over 60 kDa as measured by the MALLS method of example 2. MenW and MenY-TT conjugates were produced using sized polysaccharides of around 100-200 kDa as measured by MALLS (see example 2). Sizing was by microfluidisation using a homogenizer Emulsiflex C-50 apparatus. The polysaccharides were then filtered through a 0.2 μm filter.

Activation and coupling were performed as described in WO96/29094 and WO 00/56360. Briefly, the polysaccharide at a concentration of 10-20 mg/ml in 2M NaCl pH 5.5-6.0 was mixed with CDAPsolution (100 mg/ml freshly prepared in acetonitrile/WFI, 50/50) to a final CDAP/polysaccharide ratio of 0.75/1 or 1.5/1. After 1.5 minutes, the pH was raised with sodium hydroxide to pH10.0. After three minutes tetanus toxoid was added to reach a protein/polysaccharide ratio of 1.5/1 for MenW, 1.2/1 for MenY, 1.5/1 for MenA or 1.5/1 for MenC. The reaction continued for one to two hours.

After the coupling step, glycine was added to a final ratio of glycine/PS (w/w) of 7.5/1 and the pH was adjusted to pH9.0. The mixture was left for 30 minutes. The conjugate was clarified using a 10 μm Kleenpak® filter and was then loaded onto a Sephacryl® S400HR column using an elution buffer of 150 mM NaCl, 10 mM or 5 mM Tris pH7.5. Clinical lots were filtered on an Opticap® 4 sterilizing membrane. The resultant conjugates had an average polysaccharide:protein ratio of 1:1-1:5 (w/w).

Example 1a—Preparation of MenA and MenC Polysaccharide Conjugates of the Invention MenC-TT conjugates were produced using native polysaccharides (of over 150 kDa as measured by MALLS) or were slightly microfluidised. MenA-TT conjugates were produced using either native polysaccharide or slightly microfluidised polysaccharide of over 60 kDa as measured by the MALLS method of example 2. Sizing was by microfluidisation using a homogenizer Emulsiflex C-50 apparatus. The polysaccharides were then filtered through a 0.2 μm filter.

In order to conjugate MenA capsular polysaccharide to tetanus toxoid via a spacer, the following method was used. The covalent binding of the polysaccharide and the spacer (ADH) is carried out by a coupling chemistry by which the polysaccharide is activated under controlled conditions by a cyanylating agent, 1-cyano-4-dimethylamino-pyridinium tetrafluoroborate (CDAP). The spacer reacts with the cyanylated PS through its hydrazino groups, to form a stable isourea link between the spacer and the polysaccharide.

A 10 mg/ml solution of MenA (pH 6.0) [3.5 g] was treated with a freshly prepared 100 mg/ml solution of CDAP in acetonitrile/water (50/50 (v/v)) to obtain a CDAP/MenA ratio of 0.75 (w/w). After 1.5 minutes, the pH was raised to pH 10.0. Three minutes later, ADH was added to obtain an ADH/MenA ratio of 8.9. The pH of the solution was decreased to 8.75 and the reaction proceeded for 2 hours maintaining this pH (with temperature kept at 25° C.).

The PSAAH solution was concentrated to a quarter of its initial volume and then diafiltered with 30 volumes of 0.2M NaCl using a Filtron Omega membrane with a cut-off of 10 kDa, and the retentate was filtered.

Prior to the conjugation (carbodiimide condensation) reaction, the purified TT solution and the PSAAH solution were diluted to reach a concentration of 10 mg/ml for PSAAH and 10 mg/ml for TT.

EDAC (1-ethyl-3-(3-dimethyl-aminopropyl) carbodiimide) was added to the PSAH solution (2 g saccharide) in order to reach a final ratio of 0.9 mg EDAC/mg PSAAH. The pH was adjusted to 5.0. The purified tetanus toxoid was added with a peristaltic pump (in 60 minutes) to reach 2 mg TT/mg PSAAH. The resulting solution was left 60 min at +25° C. under stirring to obtain a final coupling time of 120 min. The solution was neutralised by addition of 1M Tris-Hcl pH 7.5 (1/10 of the final volume) and left 30 minutes at +25° C. then overnight at +2° C. to +8° C.

The conjugate was clarified using a 10 μm filter and was purified using a Sephacryl® S400HR column (Pharmacia, Sweden). The column was equilibrated in 10 mM Tris-HCl (pH 7.0), 0.075 M NaCl and the conjugate (approx. 660 mL) was loaded on the column (+2° C. to +8° C.). The elution pool was selected as a function of optical density at 280 nm. Collection started when absorbance increased to 0.05. Harvest continued until the Kd reached 0.30. The conjugate was filter sterilised at +20° C., then stored at +2° C. to +8° C. The resultant conjugate had a polysaccharide:protein ratio of 1:2-1:4 (w/w).

In order to conjugate MenC capsular polysaccharide to tetanus toxoid via a spacer, the following method was used. The covalent binding of the polysaccharide and the spacer (ADH) is carried out by a coupling chemistry by which the polysaccharide is activated under controlled conditions by a cyanylating agent, 1-cyano-4-dimethylamino-pyridinium tetrafluoroborate (CDAP). The spacer reacts with the cyanylated PS through its hydrazino groups, to form a stable isourea link between the spacer and the polysaccharide.

A 20 mg/ml solution of MenC (pH6.0) (3.5 g) was treated with a freshly prepared 100 mg/ml solution of CDAP in acetonitrile/water (50/50 (v/v)) to obtain a CDAP/MenC ratio of 1.5 (w/w). After 1.5 minutes, the pH was raised to pH 10.0. At activation pH 5M NaCl was added to achieve a final concentration of 2M NaCl. Three minutes later, ADH was added to obtain an ADH/MenC ratio of 8.9. The pH of the solution was decreased to 8.75 and the reaction proceeded for 2 hours (retained at 25° C.).

The PSCAH solution was concentrated to a minimum of 150 mL and then diafiltered with 30 volumes of 0.2M NaCl using a Filtron Omega membrane with a cut-off of 10 kDa, and the retentate was filtered.

Prior to the conjugation reaction, the purified TT solution and the PSCAH solution (2 g scale) were diluted in 0.2M NaCl to reach a concentration of 15 mg/ml for PSCAH and 20 mg/ml for TT.

The purified tetanus toxoid was added to the PSCAH solution in order to reach 2 mg TT/mg PSCAH. The pH was adjusted to 5.0. EDAC (16.7 mg/ml in Tris 0.1M pH 7.5) was added with a peristaltic pump (in 10 minutes) to reach a final ratio of 0.5 mg EDAC/mg PSCAH. The resulting solution was left 110 min at +25° C. under stirring and pH regulation to obtain a final coupling time of 120 min. The solution was then neutralized by addition of 1M Tris-Hcl pH 9.0 (1/10 of final volume) and left 30 minutes at +25° C. then overnight at +2° C. to +8° C.

The conjugate was clarified using a 10 μm filter and was purified using a Sephacryl® S400HR column (Pharmacia, Sweden). The column was equilibrated in 10 mM Tris-HCl (pH 7.0), 0.075 M NaCl and the conjugate (approx. 460 mL) was loaded on the column (+2° C. to +8° C.). The elution pool was selected as a function of optical density at 280 nm. Collection started when absorbance increased to 0.05. Harvest continued until the Kd reached 0.20. The conjugate was filter sterilised at +20° C., then stored at +2° C. to +8° C. The resultant conjugate had a polysaccharide:protein ratio of 1:2-1:4 (w/w).

Example 2—Determination of Molecular Weight Using MALLS

Detectors were coupled to a HPLC size exclusion column from which the samples were eluted. On one hand, the laser light scattering detector measured the light intensities scattered at 16 angles by the macromolecular solution and on the other hand, an interferometric refractometer placed on-line allowed the determination of the quantity of sample eluted. From these intensities, the size and shape of the macromolecules in solution can be determined.

The mean molecular weight in weight ($M_w$) is defined as the sum of the weights of all the species multiplied by their respective molecular weight and divided by the sum of weights of all the species.

a) Weight-average molecular weight: -Mw- $$M_w = \frac{\sum W_i \cdot M_i}{\sum W_i} = \frac{m_2}{m_1}$$

b) Number-average molecular weight: -Mn- $$M_n = \frac{\sum N_i \cdot M_i}{\sum N_i} = \frac{m_1}{m_0}$$

c) Root mean square radius: -Rw- and $R^2w$ is the square radius defined by:

$$R^2w \text{ or } (r^2)w = \frac{\sum m_i \cdot r_i^2}{\sum m_i}$$

(-$m_i$- is the mass of a scattering centre i and -$r_i$- is the distance between the scattering centre i and the center of gravity of the macromolecule).

d) The polydispersity is defined as the ratio -Mw/Mn-.

Meningococcal polysaccharides were analysed by MALLS by loading onto two HPLC columns (TSKG6000 and 5000PWxl) used in combination. 25 µl of the polysaccharide were loaded onto the column and was eluted with 0.75 ml of filtered water. The polyaccharides are detected using a light scattering detector (Wyatt Dawn DSP equipped with a 10 mW argon laser at 488 nm) and an inferometric refractometer (Wyatt Otilab DSP equipped with a P100 cell and a red filter at 498 nm).

The molecular weight polydispersities and recoveries of all samples were calculated by the Debye method using a polynomial fit order of 1 in the Astra 4.72 software.

Example 3—Clinical Trial Comparing Immunisation with Meningitec™ or a Larger Sized MenC-TT Conjugate A phase II, open, controlled study was carried out to compareGSK Biologicals meningococcal serogroup C conjugate vaccine (MenC) with GSK Biological's *Haemophilus influenzae* b-meningococcal serogroup C conjugate vaccine (Hib-MenC) or Meningitec™. Each dose of Meningitec™ contains 10 µg of meningococcal serogroup C oligosaccharide conjugated to 15 µg of CRM197 and is produced by Wyeth. The GSK MenC conjugates contained native polysaccharides of about 200 kDa conjugated to tetanus toxoid (TT).

The study consisted of five groups, each planned to contain 100 subjects, allocated to two parallel arms as follows:

In this present study, all subjects in both arms received one-fifth (⅕) of a dose of Mencevax™ ACWY and a concomitant dose of Infanrix™ hexa at 12-15 months of age (Study Month 0). Two blood samples were collected from all subjects (Study Month 0 and Study Month 1). Arm 1 consisted of four groups from a primary vaccination study who were primed at their age of 3, 4 and 5 months with the following vaccines:

Group K: MenC (10 µg), non-adsorbed (non-ads), tetanus toxoid (TT) conjugate and Infanrix™ hexa (MenC10-TT+Infanrix™ hexa)

Group L: Hib (10 µg)-MenC (10 µg), non-ads TT conjugate and Infanrix™ penta (Hib10-MenC10-TT+Infanrix™ penta)

Group M: Hib (5 µg)-MenC (5 µg), non-ads, TT conjugate and Infanrix™ penta (Hib5-MenC5-TT+Infanrix™ penta)

Group N: Meningitec™ and Infanrix™ hexa (Meningitec™+Infanrix™ hexa)

The two Hib-MenC-TT vaccine groups (Groups L and M) were kept blinded in the booster study as to the exact formulation of the candidate vaccine.

Arm 2-(Group O) consisted of age-matched subjects not previously vaccinated with a meningococcal serogroup C vaccine (naïve) but who had received routine pediatric vaccines according to the German Permanent Commission on Immunization.

Criteria for Evaluation:

Immunogenicity:

Determination of bactericidal antibody titers against meningococcal C (SBA-MenC) by a bactericidal test (cut-off: a dilution of 1:8) and ELISA measurement of antibodies against meningococcal serogroup C (assay cut-off: 0.3 µg/ml), the Hib polysaccharide PRP (assay cut-off: 0.15 µg/ml) and tetanus toxoid (assay cut-off: 0.1 IU/ml) in blood samples obtained prior to vaccination and approximately one month after vaccination in all subjects.

Statistical Methods:

Demographics:

Determination of mean age in months (with median, range and standard deviation [SD]), and racial and gender composition of the ATP and Total vaccinated cohorts.

Immunogenicity:

Two analyses of immunogenicity were performed based on the ATP cohort for immunogenicity (for analyses of immune memory and booster response) or the ATP cohort for safety (for analysis of persistence). These included: Evaluation of immune memory for MenC and booster response for Hib and Tetanus (before and one month after administration of ⅕ dose of the plain polysaccharide vaccine):

Determination of geometric mean titers and concentrations (GMTs and GMCs) with 95% confidence intervals (95% CI)

Determination of the percentage of subjects with antibody titer/concentration above the proposed cutoffs with exact 95% CI (seropositivity/seroprotection rates)

Investigation of antibody titers/concentration after vaccination using reverse cumulative curves Computation of standardized asymptotic 95% CI for the difference in seropositivity/seroprotection rate between the primed group (Groups K, L, M and N) and the unprimed group (Group O)

Determination of the geometric mean of individual ratio of SBA-MenC titer over anti-PSC concentration, with 95% CI Determination of the 95% CI for the post-vaccination GMT/C ratio between the groups K, L, M and the control group N for anti-PRP and anti-tetanus and between each primed group (Groups K, L, M and N) and the unprimed group (Group O) for SBA-MenC and anti-PSC using an ANOVA model Results

TABLE 1

SBA-MenC titres and anti-PSC antibody concentration after booster vaccination

| Antibody | Group | N | GMT/C | 95% CL LL | 95% CL UL |
|---|---|---|---|---|---|
| SBA-MenC | K-MenC-TT | 71 | 3508.9 | 2580.1 | 4772.2 |
| | L-HibMenC | 79 | 2530.1 | 1831.7 | 3494.7 |
| | M-HibMenC ™ | 81 | 5385.4 | 4425.0 | 6554.2 |
| | N-Meningitec | 85 | 1552.6 | 1044.4 | 2307.9 |
| | O-Control | 91 | 9.3 | 6.3 | 13.6 |
| Anti-PSC | K-MenC-TT | 70 | 28.10 | 22.59 | 34.95 |
| | L-HibMenC | 71 | 30.01 | 24.09 | 37.38 |
| | M-HibMenC ™ | 76 | 34.58 | 29.10 | 41.09 |
| | N-Meningitec | 78 | 16.59 | 12.98 | 21.21 |
| | O-Control | 94 | 3.05 | 2.36 | 3.93 |

Group K: subjects primed with MenC10-TT + Infanrix ™ hexa;
Group L: subjects primed with Hib10-MenC10-TT + Infanrix ™ penta;
Group M: subjects primed with Hib5-MenC5-TT + Infanrix ™ penta;
Group N: subjects primed with Meningitec ™ + Infanrix ™ hexa;
Group O: control subjects (i.e. subjects not primed with MenC conjugate vaccine)
N: number of subjects with available results Higher titres of antibodies against MenC and higher SBA titres were achieved by priming with the larger sized MenC polysaccharide conjugate vaccines (groups K, L and M) compared with the Meningitec™ oligosaccharide conjugate vaccine.

TABLE 2

Geometric mean ratio for SBA MenC titre/anti-PSC concentration

| Group | Timing | N | GMR | LL | UL |
|---|---|---|---|---|---|
| K | Pre | 70 | 49.470 | 34.939 | 70.044 |
| | Post | 66 | 126.138 | 101.419 | 156.882 |
| L | Pre | 76 | 36.528 | 25.849 | 51.621 |
| | Post | 70 | 90.200 | 70.153 | 115.975 |
| M | Pre | 77 | 51.298 | 36.478 | 72.139 |
| | Post | 74 | 164.950 | 139.304 | 195.318 |
| N | Pre | 84 | 22.571 | 16.521 | 30.837 |
| | Post | 76 | 90.168 | 67.757 | 119.991 |
| O | Pre | 3 | 91.634 | 0.651 | 12889.8 |
| | Post | 87 | 2.708 | 1.767 | 4.149 |

In all four primed groups (Groups K, L, M and N), the GMR increased significantly from pre to post booster vaccination indicating the presence of antibody maturation and functionality. GMR in the Group M (primed with Hib5-MenC5-TT) was higher than in the Group N (primed with Meningitec™)

TABLE 3

Persistence at 12-15 months of age just prior to administration of the booster vaccines

| Endpoints | Group | N | % | Group | N | % | Difference | Value % |
|---|---|---|---|---|---|---|---|---|
| SBAMenC ≥1:8 | K | 79 | 88.6 | N | 91 | 80.2 | N − K | −8.4 |
| | L | 84 | 93.3 | N | 91 | 80.2 | N − L | −3.1 |
| | M | 85 | 87.1 | N | 91 | 80.2 | N − M | −6.8 |
| SBAMenC ≥1:128 | K | 79 | 65.8 | N | 91 | 51.6 | N − K | −14.2 |
| | L | 84 | 56.0 | N | 91 | 51.6 | N − L | −4.3 |
| | M | 85 | 64.7 | N | 91 | 51.6 | N − M | −13.1 |
| Anti-PSC ≥0.3 µg/ml | K | 79 | 100.0 | N | 91 | 100.0 | N − K | 0.0 |
| | L | 84 | 100.0 | N | 91 | 100.0 | N − L | 0.0 |
| | M | 88 | 98.9 | N | 91 | 100.0 | N − M | 1.1 |
| Anti-PSC ≥2 µg/ml | K | 79 | 72.2 | N | 91 | 81.3 | N − K | 9.2 |
| | L | 84 | 64.3 | N | 91 | 81.3 | N − L | 17.0 |
| | M | 88 | 64.3 | N | 91 | 81.3 | N − M | 8.6 |
| Anti-PRP ≥0.15 µg/ml | K | 81 | 88.9 | N | 91 | 85.7 | N − K | −3.2 |
| | L | 86 | 96.5 | N | 91 | 85.7 | N − L | −10.8 |
| | M | 90 | 98.9 | N | 91 | 85.7 | N − M | −13.2 |
| Anti-PRP ≥1 µg/ml | K | 81 | 33.3 | N | 91 | 28.6 | N − K | −4.8 |
| | L | 86 | 55.8 | N | 91 | 28.6 | N − L | −27.2 |
| | M | 90 | 74.4 | N | 91 | 28.6 | N − M | −45.9 |
| Anti-tetanus ≥0.1 IU/ml | K | 81 | 100.0 | N | 91 | 96.7 | N − K | −3.3 |
| | L | 86 | 100.0 | N | 91 | 96.7 | N − L | −3.3 |
| | M | 90 | 100.0 | N | 91 | 96.7 | N − M | −3.3 |

Group K: subjects primed with MenC10-TT + Infanrix ™ hexa;
Group L: subjects primed with Hib10-MenC10-TT + Infanrix ™ penta;
Group M: subjects primed with Hib5-MenC5-TT + Infanrix ™ penta;
Group N: subjects primed with Meningitec ™ + Infanrix ™ hexa;
N: number of subjects with available results
Higher SBA titres against MenC were achieved by priming with the larger size of MenC (groups K, L and M) compared to priming with the MenC-oligosaccharide conjugate Meningitec ™.

Immune Memory (ATP Cohort for Immunogenicity)

Administration of ⅕ dose of the plain polysaccharide ACWY vaccine elicited very high SBA-MenC titer in all four primed groups with 98.7-100% and 97.5-100% of subjects primed with a candidate vaccine regimen exhibiting titers ≥1:8 and ≥1:128, respectively. In the group primed with the Meningitec™ regimen, there was a trend for a lower percentage of subjects with titers ≥1:128 (91.8%). In comparison, 17.6% of unprimed subjects had SBA MenC titers ≥1:8 and ≥1:128.

Example 4—Phase II Clinical Trial on HibMenAC-TT Conjugate Vaccine Mixed with DTPw-HepB Study Design:

Open, randomized (1:1:1:1:1), single centre study with five groups. The five groups received the following vaccination regimen respectively, at 6, 10 and 14 weeks of age.

Tritanrix™-HepB/Hib-MenAC 2.5/2.5/2.5: henceforth referred to as 2.5/2.5/2.5

Tritanrix™-HepB/Hib-MenAC 2.5/5/5: henceforth referred to as 2.5/5/5

Tritanrix™-HepB/Hib-MenAC 5/5/5: henceforth referred to as 5/5/5

Tritanrix™-HepB+Hiberix™ henceforth referred to as Hiberix

Tritanrix™ HepB/Hiberix™+Meningitec™: henceforth referred to as Meningitec™

Blood samples were taken at the time of the first vaccine dose (Pre) and one month after the third vaccine dose (Post-dose 3).

Tritanrix™ is a DTPw vaccine marketed by GlaxoSmithKline Biologicals S.A.

105 subjects were used in each of the five groups giving a total of 525 subjects in the study.

TABLE 4

Content of GSK vaccine formulations

| Components per dose (0.5 ml) | 2.5/2.5/2.5* | 2.5/5/5 | 5/5/5 |
|---|---|---|---|
| Hib capsular polysaccharide PRP conjugated to tetanus toxoid (TT) | 2.5 µg | 2.5 µg | 5 µg |

TABLE 4-continued

Content of GSK vaccine formulations

| Components per dose (0.5 ml) | 2.5/2.5/2.5* | 2.5/5/5 | 5/5/5 |
|---|---|---|---|
| *Neisseria meningitidis* A capsular polysaccharide (PSA) conjugated to TT | 2.5 μg | 5 μg | 5 μg |
| *Neisseria meningitidis* C capsular polysaccharide (PSC) conjugated to TT | 2.5 μg | 5 μg | 5 μg |

*The 2.5/2.5/2.5 vaccine was a dose dilution of GSK Biologicals' Hib-MenAC 5/5/5 vaccine containing 2.5 μg of each of PRP-TT, MenA-TT and MenC-TT.

The Hib-MenAC vaccine formulations were mixed extemporaneously with Tritanirix™-HepB. GSK Biologicals' combined diphtheria-tetanus-whole cell *Bordetella pertussis*-hepatitis B (DTPw-HB) vaccine (Tritanrix™-HepB) contains not less than 30 International Units (IU) of diphtheria toxoid, not less than 60 IU of tetanus toxoid, not less than 4 IU of killed *Bordetella pertussis* and 10 μg of recombinant hepatitis B surface antigen.

Reference Therapy, Dose, Mode of Administration, Lot No.:

Vaccination Schedule/Site:

One group received Tritanrix™ HepB vaccine intramuscularly in the left thigh and Hiberix™ intramuscularly in the right thigh at 6, 10 and 14 weeks of age. Another group received Tritanrix™ HepB/Hiberix® vaccine intramuscularly in the left thigh and Meningitec™ vaccine intramuscularly in the right thigh at 6, 10 and 14 weeks of age.

Vaccine/Composition/Dose/Lot Number:

The Tritanrix™ HepB vaccine used was as described above.

One dose (0.5 ml) of GSK Biologicals' *Haemophilus influenzae* type b conjugate vaccine: Hiberix™ contained 10 μg of PRP conjugated to tetanus toxoid. In the Hiberix™ Group, it was mixed with sterile diluent and in the Meningitec™ Group it was mixed with Tritanrix™-HepB.

One dose (0.5 ml) of Wyeth Lederle's MENINGITEC™ vaccine contained: 10 μg of capsular oligosaccharide of meningococcal group C conjugated to 15 μg of *Corynebacterium diphtheria* CRM197 protein and aluminium as salts.

Results—Immune Responses Generated Against Hib, MenA and MenC

TABLE 5a

Anti-PRP (μg/ml)

| | 2.5/2.5/2.5 Group | | | 2.5/5/5 | | | 5/5/5 | | | Hiberix™ | | | Meningitec™ | | |
|---|---|---|---|---|---|---|---|---|---|---|---|---|---|---|---|
| | % GMC/T | 95% CL LL | UL | % GMC/T | 95% CL LL | UL | % GMC/T | 95% CL LL | UL | % GMC/T | 95% CL LL | UL | % GMC/T | 95% CL LL | UL |
| % ≥0.15 | 100 | 96.5 | 100 | 99.0 | 94.8 | 100 | 100 | 96.5 | 100 | 100 | 96.5 | 100 | 100 | 96.5 | 100 |
| GMC | 20.80 | 15.96 | 27.10 | 22.62 | 17.72 | 28.88 | 19.36 | 15.33 | 24.46 | 38.55 | 29.93 | 49.64 | 10.94 | 8.62 | 13.88 |

TABLE 5b

SBA-MenC

| | 2.5/2.5/2.5 Group | | | 2.5/5/5 | | | 5/5/5 | | | Hiberix™ | | | Meningitec™ | | |
|---|---|---|---|---|---|---|---|---|---|---|---|---|---|---|---|
| | % GMC/T | 95% CL LL | UL | % GMC/T | 95% CL LL | UL | % GMC/T | 95% CL LL | UL | % GMC/T | 95% CL LL | UL | % GMC/T | 95% CL LL | UL |
| % ≥1:8 | 99 | 94.7 | 100 | 100 | 96.5 | 100 | 100 | 96.5 | 100 | 2.9 | 0.6 | 8.4 | 100 | 96.5 | 100 |
| GMT | 3132 | 2497 | 3930 | 4206 | 3409 | 5189 | 3697 | 3118 | 4384 | 4.7 | 3.9 | 5.6 | 4501 | 3904 | 5180 |

TABLE 5c

SBA MenA

| | 2.5/2.5/2.5 Group | | | 2.5/5/5 | | | 5/5/5 | | | Hiberix™ | | | Meningitec™ | | |
|---|---|---|---|---|---|---|---|---|---|---|---|---|---|---|---|
| | % GMC/T | 95% CL LL | UL | % GMC/T | 95% CL LL | UL | % GMC/T | 95% CL LL | UL | % GMC/T | 95% CL LL | UL | % GMC/T | 95% CL LL | UL |
| % ≥1:8 | 99.7 | 91.9 | 99.7 | 100 | 95.8 | 100 | 100 | 96.2 | 100 | 6.8 | 2.5 | 14.3 | 9.1 | 4.0 | 17.1 |
| GMT | 316.7 | 251.4 | 398.9 | 418.5 | 358.6 | 488.5 | 363 | 310.5 | 424.4 | 5.6 | 4.3 | 7.4 | 5.6 | 4.4 | 7.2 |

TABLE 5d

Anti-PSC (μg/ml)

| | Group | | | | | | | | | | | | | | |
|---|---|---|---|---|---|---|---|---|---|---|---|---|---|---|---|
| | 2.5/2.5/2.5 | | | 2.5/5/5 | | | 5/5/5 | | | Hiberix ™ | | | Meningitec ™ | | |
| | % | 95% CL | | % | 95% CL | | % | 95% CL | | % | 95% CL | | % | 95% CL | |
| | GMC/T | LL | UL | GMC/T | LL | UL | GMC/T | LL | UL | GMC/T | LL | UL | GMC/T | LL | UL |
| % ≥0.3 | 100 | 96.5 | 100 | 100 | 96.4 | 100 | 100 | 96.5 | 100 | 8.2 | 3.6 | 15.6 | 100 | 96.5 | 100 |
| GMC | 49.03 | 43.24 | 55.59 | 71.11 | 62.49 | 80.92 | 61.62 | 54.88 | 69.20 | 0.17 | 0.15 | 0.19 | 58.02 | 51.42 | 65.46 |

TABLE 5e

Anti-PSA (μg/ml)

| | Group | | | | | | | | | | | | | | |
|---|---|---|---|---|---|---|---|---|---|---|---|---|---|---|---|
| | 2.5/2.5/2.5 | | | 2.5/5/5 | | | 5/5/5 | | | Hiberix ™ | | | Meningitec ™ | | |
| | % | 95% CL | | % | 95% CL | | % | 95% CL | | % | 95% CL | | % | 95% CL | |
| | GMC/T | LL | UL | GMC/T | LL | UL | GMC/T | LL | UL | GMC/T | LL | UL | GMC/T | LL | UL |
| % ≥0.3 | 100 | 96.4 | 100 | 100 | 96.5 | 100 | 99.0 | 94.8 | 100 | 1.0 | 0.0 | 5.4 | 5.9 | 2.2 | 12.5 |
| GMC | 18.10 | 15.34 | 21.35 | 26.51 | 22.93 | 30.79 | 23.40 | 20.05 | 27.30 | 0.15 | 0.15 | 0.15 | 0.17 | 0.15 | 0.18 |

Conclusion

A comparison of the immunogenicity results achieved using the oligosaccharide MenC-CRM197 conjugate vaccine and the three GSK formulations which contain polysaccharide MenA-TT and MenC-TT conjugates showed that the polysaccharide Men conjugates were able to elicit a good immunogenic response similar to that achieved using the oligosaccharide conjugate vaccine Meningitec™. All formulations tested gave a response to MenC in 100% of patients.

Example 5—Phase II Clinical Trial Administering Hib MenCY Concomitantly with Infanrix™ Penta According to a 2, 3 and 4 Month Schedule Study Design:

A Phase II, open (partially double-blind*) randomized controlled multi-center study with 5 groups receiving a three-dose primary schedule with vaccines as follows:

Group Hib-MenCY 2.5/5/5: Hib-MenCY (2.5/5/5)+Infanrix™ penta
Group Hib-MenCY 5/10/10: Hib-MenCY (5/10/10)+Infanrix™ penta
Group Hib-MenCY 5/5/5: Hib-MenCY (5/5/5)+Infanrix™ penta
Group Hib-MenC: Hib-MenC (5/5)+Infanrix™ penta
Group Menjugate: Menjugate™**+Infanrix™ hexa (control).

*Hib-MenCY 2.5/5/5, Hib-MenCY 5/10/10 and Hib-MenC were administered in a double-blind manner while the Hib-MenCY 5/5/5 group and the Menjugate group were open. The 2.5/5/5, 5/10/10 and 5/5/5 formulations of Hib-MenCY contain MenC native polysaccharides and MenY polysaccharides which are microfluidized.

**Menjugate™ contains 10 μg of MenC oligosaccharides conjugated to 12.5-25 μg of CRM197 per dose and is produced by Chiron.

Vaccination at +/−2, 3, 4 months of age (Study Month 0, Month 1 and Month 2), and blood samples (3.5 ml) from all subjects prior to and one month post primary vaccination (Study Month 0 and Month 3).

Study Vaccine, Dose, Mode of Administration, Lot Number:

Three doses injected intramuscularly at one month intervals, at approximately 2, 3 and 4 months of age as follows:

TABLE 6

Vaccines administered (study and control), group, schedule/site and dose

| Group | Schedule (months of age) | Vaccine dose administered Site - Left upper thigh | Concomitant vaccine administered Site Right upper thigh |
|---|---|---|---|
| Hib-MenCY 2.5/5/5 | 2, 3, and 4 | Hib (2.5 μg)-MenC-TT (5 μg)-MenY-TT (5 μg) | DTPa-HBV-IPV (Infanrix ™ penta) |
| Hib-MenCY 5/10/10 | 2, 3, and 4 | Hib (5 μg)-MenC-TT (10 μg)-MenY-TT (10 μg) | DTPa-HBV-IPV (Infanrix ™ penta) |
| Hib-MenCY 5/5/5 | 2, 3, and 4 | Hib (5 μg)-MenC-TT (5 μg)-MenY-TT (5 μg) | DTPa-HBV-IPV (Infanrix ™ penta) |
| Hib-MenC | 2, 3, and 4 | Hib (5 μg)-Men C (5 μg) | DTPa-HBV-IPV (Infanrix ™ penta) |
| Menjugate ™ | 2, 3, and 4 | Menjugate ™ | DTPa-HBV-IPV/Hib (Infanrix ™hexa) |

Immunogenicity:

Measurement of antibody titres/concentrations against each vaccine antigen:

Prior to the first dose (Month 0) and approximately one month after the third dose (Month 3) in all subjects for: SBA-MenC and SBA-MenY, anti-PSC and anti-PSY, anti-PRP, anti-T, anti-FHA, anti-PRN and anti-PT. Using serum bactericidal activity against N. meningitidis serogroups C and Y (SBA-MenC and SBA-MenY cut-off: 1:8 and 1:128); ELISA assays with cut-offs: ≥0.3 μg/ml and ≥2 μg/ml for anti-N. meningitidis serogroups C and Y polysaccharides (anti-PSC IgG and anti-PSY IgG); ≥0.15 μg/ml and ≥1.0 μg/ml for Hib polysaccharide polyribosil-ribitol-phosphate (anti-PRP IgG); 5EL.U/ml for anti-FHA, anti-PRN, anti-PT; ≥0.1 IU/ml anti-tetanus toxoid (anti-TT). Only at one month after the third dose (Month 3) in all subjects for: anti-D, anti-HBs and anti-polio 1, 2 and 3. Using ELISA assays with cut-offs: 0.1 IU/ml for anti-diphtheria (anti-D); 0 mIU/ml for antihepatitis B (anti-HBs); and microneutralization test cut-off: 1:8 for anti-polio type 1, 2 and 3 (anti-polio 1, 2 and 3).

Statistical Methods:

The seroprotection/seropositivity rates and geometric mean concentrations/titres (GMCs/GMTs) with 95% confidence intervals (95% CI) were computed per group, for SBA-MenC, anti-PSC, SBA-MenY, anti-PSY, anti-PRP, anti-Tetanus, anti-PT, anti-FHA and anti-PRN prior to and one month after vaccination; for anti-Diphtheria, anti-HBs, anti-Polio 1, anti-Polio 2 and anti-Polio 3 one month after vaccination. Vaccine response (appearance of antibodies in subjects initially seronegative or at least maintenance of antibody concentrations in subjects initially seropositive) with 95% CI for anti-PT, anti-PRN and anti-FHA were also computed one month after vaccination. Reverse cumulative curves for each antibody at Month 3 are also presented. The differences between the Hib-MenCY and the Hib-MenC groups, compared with the Menjugate™ control group were evaluated in an exploratory manner for each antibody, except for SBA-MenY and anti-PSY, in terms of (1) the difference between the Menjugate™ group (minus) the Hib-MenCY and Hib-MenC groups for the percentage of subjects above the specified cut-offs or with a vaccine response with their standardized asymptotic 95% CI, (2) the GMC or GMT ratios of the Menjugate™ group over the Hib-MenCY and Hib-MenC groups with their 95% CI. The same comparisons were done to evaluate the difference between each pair of Hib-MenCY formulations for anti-PRP, SBA-MenC, anti-PSC, SBA-MenY, anti-PSY and anti-TT antibodies.

The overall incidences of local and general solicited symptoms were computed by group according to the type of symptom, their intensity and relationship to vaccination (as percentages of subjects reporting general, local, and any solicited symptoms within the 8 days following vaccination and their exact 95% CI). Incidences of unsolicited symptoms were computed per group. For Grade 3 symptoms, onset 48 hours, medical attention, duration, relationship to vaccination and outcomes were provided. Serious Adverse Events were fully described.

Seroprotection/Seropositivity Rates &GMC/Ts (ATP Cohort for Immunogenicity)

TABLE 7a

Anti-PRP (μg/ml)

| Group | N | % ≥0.15 | LL | UL | ≥1 | LL | UL | GMC | LL | UL |
|---|---|---|---|---|---|---|---|---|---|---|
| Hib MenCY 2.5/5/5 | 67 | 100.0 | 94.6 | 100.0 | 98.5 | 92.0 | 100.0 | 9.01 | 7.25 | 11.21 |
| Hib MenCY 5/10/10 | 67 | 100.0 | 94.6 | 100.0 | 98.5 | 92.0 | 100.0 | 9.49 | 7.72 | 11.65 |
| Hib MenCY 5/5/5 | 70 | 100.0 | 94.9 | 100.0 | 98.6 | 92.3 | 100.0 | 8.08 | 6.53 | 9.98 |
| Hib MenC | 74 | 100.0 | 95.1 | 100.0 | 98.6 | 92.7 | 100.0 | 10.44 | 8.49 | 12.83 |
| Menjugate ™ | 71 | 100.0 | 94.9 | 100.0 | 80.3 | 69.1 | 88.8 | 2.60 | 1.97 | 3.43 |

TABLE 7b

SBA-MenC (Titre)

| Group | N | % ≥1:8 | LL | UL | ≥1:128 | LL | UL | GMT | LL | UL |
|---|---|---|---|---|---|---|---|---|---|---|
| Hib MenCY 2.5/5/5 | 70 | 100.0 | 94.9 | 100.0 | 95.7 | 88.0 | 99.1 | 1005.8 | 773.5 | 1308.0 |
| Hib MenCY 5/10/10 | 67 | 100.0 | 94.6 | 100.0 | 94.0 | 85.4 | 98.3 | 1029.8 | 799.7 | 1326.0 |
| Hib MenCY 5/5/5 | 71 | 100.0 | 94.9 | 100.0 | 94.4 | 86.2 | 98.4 | 906.9 | 691.3 | 1189.8 |
| Hib MenC | 74 | 100.0 | 95.1 | 100.0 | 95.9 | 88.6 | 99.2 | 871.0 | 677.3 | 1120.0 |
| Menjugate ™ | 71 | 100.0 | 94.9 | 100.0 | 100.0 | 94.9 | 100.0 | 3557.6 | 2978.8 | 4248.8 |

TABLE 7c

Anti-PSC (μg/ml)

| Group | N | % ≥0.3 | LL | UL | ≥2 | LL | UL | GMC | LL | UL |
|---|---|---|---|---|---|---|---|---|---|---|
| Hib MenCY 2.5/5/5 | 69 | 100.0 | 94.8 | 100.0 | 100.0 | 94.8 | 100.0 | 21.70 | 18.36 | 25.65 |
| Hib MenCY 5/10/10 | 66 | 100.0 | 94.6 | 100.0 | 100.0 | 94.6 | 100.0 | 27.26 | 23.26 | 31.95 |
| Hib MenCY 5/5/5 | 70 | 100.0 | 94.9 | 100.0 | 100.0 | 94.9 | 100.0 | 19.02 | 16.49 | 21.93 |
| Hib MenC | 74 | 100.0 | 95.1 | 100.0 | 100.0 | 95.1 | 100.0 | 21.08 | 18.24 | 24.35 |
| Menjugate ™ | 71 | 100.0 | 94.9 | 100.0 | 100.0 | 94.9 | 100.0 | 38.49 | 33.64 | 44.05 |

TABLE 7d

SBA-MenY (Titre)

| Group | N | % ≥1:8 | LL | UL | ≥1:128 | LL | UL | GMT | LL | UL |
|---|---|---|---|---|---|---|---|---|---|---|
| Hib MenCY 2.5/5/5 | 69 | 97.1 | 89.9 | 99.6 | 92.8 | 83.9 | 97.6 | 470.7 | 351.1 | 631.2 |
| Hib MenCY 5/10/10 | 66 | 97.0 | 89.5 | 99.6 | 86.4 | 75.7 | 93.6 | 437.1 | 322.0 | 593.4.8 |
| Hib MenCY 5/5/5 | 71 | 98.6 | 92.4 | 100.0 | 95.8 | 88.1 | 99.1 | 635.3 | 501.5 | 804.8 |
| Hib MenC | 74 | 21.6 | 12.9 | 32.7 | 13.5 | 6.7 | 23.5 | 9.3 | 6.3 | 13.7 |
| Menjugate ™ | 71 | 19.7 | 11.2 | 30.9 | 9.9 | 4.1 | 19.3 | 7.5 | 5.4 | 10.4 |

TABLE 7e

Anti-PSY (μg/ml)

| Group | N | % ≥0.3 | LL | UL | ≥2 | LL | UL | GMC | LL | UL |
|---|---|---|---|---|---|---|---|---|---|---|
| Hib MenCY 2.5/5/5 | 69 | 100.0 | 94.8 | 100.0 | 100.0 | 94.8 | 100.0 | 26.86 | 22.86 | 31.56 |
| Hib MenCY 5/10/10 | 66 | 100.0 | 94.6 | 100.0 | 100.0 | 94.6 | 100.0 | 37.02 | 31.84 | 43.04 |
| Hib MenCY 5/5/5 | 70 | 100.0 | 94.9 | 100.0 | 100.0 | 94.9 | 100.0 | 23.57 | 19.94 | 27.86 |
| Hib MenC | 74 | 8.1 | 3.0 | 16.8 | 4.1 | 0.8 | 11.4 | 0.19 | 0.15 | 0.25 |
| Menjugate ™ | 71 | 5.6 | 1.6 | 13.8 | 1.4 | 0.0 | 7.6 | 0.17 | 0.15 | 0.19 |

TABLE 7f

Anti-tetanus (IU/ml)

| Group | N | % ≥0.1 | LL | UL | GMC | LL | UL |
|---|---|---|---|---|---|---|---|
| Hib MenCY 2.5/5/5 | 68 | 100.0 | 94.7 | 100.0 | 3.06 | 2.63 | 3.55 |
| Hib MenCY 5/10/10 | 67 | 100.0 | 94.6 | 100.0 | 3.25 | 2.88 | 3.68 |
| Hib MenCY 5/5/5 | 70 | 100.0 | 94.9 | 100.0 | 2.97 | 2.59 | 3.41 |
| Hib MenC | 74 | 100.0 | 95.1 | 100.0 | 3.15 | 2.73 | 3.64 |
| Menjugate ™ | 71 | 100.0 | 94.9 | 100.0 | 1.66 | 1.39 | 1.97 |

Group Hib-MenCY 2.5/5/5: Hib-MenCY (2.5/5/5) + Infanrix ™ penta
Group Hib-MenCY 5/10/10: Hib-MenCY (5/10/10) + Infanrix ™ penta
Group Hib-MenCY 5/5/5: Hib-MenCY (5/5/5) + Infanrix ™ penta
Group Hib-MenC: Hib-Men (5/5) + Infanrix ™ hexa
Group Menjugate: Menjugate ™ + Infanrix ™ penta
N = number of subjects with available results.
% = percentage of subjects with concentration/titre within the specificed range
GMC/T: geometric mean concentration/titre
95% CI = 95% confidence interval;
LL = Lower Limit;
UL = Upper Limit Conclusion The MenC and Y polysaccharide conjugates produced a good immune response in all subjects with 100% of subjects producing above 0.3 μg/ml responses against MenC and MenY.

Example 6—Phase II Clinical Trial Comparing Three Formulations of MenACWY-TT with Meningitec™ MenC-CRM197 Oligosaccharide-Conjugate Vaccine This example reports a phase II, open (partially-blind), randomized, controlled dose-range study to evaluate the Immunogenicity of three different formulations of GlaxoSmithKline Biological's meningococcal serogroups A, C, W-135, Y tetanus toxoid conjugate (MenACWY-TT) vaccine in comparison to a MenC oligosaccharide-CRM197 conjugate vaccine (Meningitec™) when given as one dose to children aged 12-14 months.

The clinical trial was an open (partially double-blind*), controlled, multicentric study in which eligible subjects of 12-14 months were randomized (1:1:1:1) to one of four parallel groups of 50 subjects to receive a single primary dose at Visit 1 as follows:

Form 1T: MenACWY-TT at a dose of 2.5 μg of MenA polysaccharide conjugated to tetanus toxoid (TT), 2.5 μg of MenC polysaccharide conjugated to TT, 2.5 μg of MenW polysaccharide conjugated to TT and 2.5 μg of MenY polysaccharide conjugated to TT.

Form 2T: MenACWY-TT at a dose of 5 μg of MenA polysaccharide conjugated to TT, 5 μg of MenC polysaccharide conjugated to TT, 5 μg of MenW polysaccharide conjugated to TT and 5 μg of MenY polysaccharide conjugated to TT.

Form 3T: MenACWY-TT at a dose of 2.5 μg of MenA polysaccharide conjugated to TT, 10 μg of MenC polysaccharide conjugated to TT, 2.5 μg of MenW polysaccharide conjugated to TT and 2.5 μg of MenY polysaccharide conjugated to TT.

Ctrl T: 10 μg MenC oligosaccharide conjugated to 12.5-25 μg CRM197 (Meningitec).

*The three different MenACWY-TT formulations were administered in a double-blind manner.

Vaccination Schedule/Site:

A single vaccine dose was administered intramuscularly in the left deltoid at Visit 1 (Study Month 0) according to randomized assignment. All candidate vaccines were supplied as a lyophilized pellet in a monodose vial (0.5 ml after reconstitution with the supplied saline diluent).

Immunogenicity:

Measurement of titers/concentrations of antibodies against meningococcal vaccine antigen components in blood samples obtained prior to the study vaccine dose (Month 0) and approximately one month after the study vaccine dose (Month 1) in all subjects. Determination of bactericidal antibody titers against N. meningitidis serogroups A, C, W-135 and Y (SBA-MenA, SBA-MenC, SBA-MenW and SBA-MenY) by a bactericidal test (assay cut-offs: a dilution of 1:8 and 1:128) and ELISA measurement of antibodies against N. meningitidis serogroups A, C, W-135 and Y (anti-PSA, anti-PSC, anti-PSW and anti-PSY, assay cut-offs ≥0.3 μg/ml and ≥2 μg/ml), and tetanus toxoid (anti-tetanus, assay cut-off 0.1 IU/ml).

Results

Antibody response in terms of the percentage of SBA-MenA, SBA-MenC, SBA-MenW and SBA-MenY responders one month after vaccination (the primary endpoint) is shown in Table 8. A response is defined as greater than or equal to a 4-fold increase for seropositive subjects or seroconversion for seronegative subjects before vaccination.

TABLE 8

Vaccine responses for SBA antibody one month after vaccination

| Antibody | Group | N | % | LL | UL |
|---|---|---|---|---|---|
| SBA-MenA | Form 1T | 42 | 61.9 | 45.6 | 76.4 |
|  | Form 2T | 39 | 82.1 | 66.5 | 92.5 |
|  | Form 3T | 40 | 62.5 | 45.8 | 77.3 |
|  | Meningitec ™ | 36 | 11.1 | 3.1 | 26.1 |
| SBA-MenC | Form 1T | 46 | 97.8 | 88.5 | 99.9 |
|  | Form 2T | 43 | 100.0 | 91.8 | 100.0 |
|  | Form 3T | 44 | 95.5 | 84.5 | 99.4 |
|  | Meningitec ™ | 49 | 91.8 | 80.4 | 97.7 |
| SBA-MenW | Form 1T | 45 | 100.0 | 92.1 | 100.0 |
|  | Form 2T | 43 | 97.7 | 87.7 | 99.9 |
|  | Form 3T | 45 | 100.0 | 92.1 | 100.0 |
|  | Meningitec ™ | 46 | 15.2 | 6.3 | 28.9 |
| SBA-MenY | Form 1T | 47 | 97.9 | 88.7 | 99.9 |
|  | Form 2T | 44 | 88.6 | 75.4 | 96.2 |
|  | Form 3T | 45 | 93.3 | 81.7 | 98.6 |
|  | Meningitec ™ | 49 | 4.1 | 0.5 | 14.0 |

Table 9 shows the numbers of subjects achieving SBA titres over cutoff points of 1:8 and 1:128 as well as GMTs.

TABLE 9

Seropositivity rates and GMTs for SBA antibodies one month after vaccination

|  | Group | N | ≥1:8 % | LL | UL | ≥1:128 % | LL | UL | GMT |
|---|---|---|---|---|---|---|---|---|---|
| SBA-MenA | Form 1T | 46 | 100 | 92.3 | 100 | 100 | 92.3 | 100 | 1457.3 |
|  | Form2T | 45 | 100 | 92.1 | 100 | 97.8 | 88.2 | 99.9 | 1776.9 |
|  | Form3T | 48 | 97.9 | 88.9 | 99.9 | 97.9 | 88.9 | 99.9 | 1339.5 |
|  | Meningitec ™ | 41 | 51.2 | 35.1 | 67.1 | 43.9 | 28.5 | 60.3 | 42.8 |
| SBA-MenC | Form 1T | 47 | 97.9 | 88.7 | 99.9 | 78.7 | 64.3 | 89.3 | 281.3 |
|  | Form2T | 45 | 100 | 92.1 | 100 | 84.4 | 70.5 | 93.5 | 428.6 |
|  | Form3T | 47 | 95.7 | 85.5 | 99.5 | 85.1 | 71.7 | 93.8 | 478.4 |
|  | Meningitec ™ | 50 | 94.0 | 83.5 | 98.7 | 62.0 | 47.2 | 75.3 | 200.1 |
| SBA-MenW | Form 1T | 47 | 100 | 92.5 | 100 | 100 | 92.5 | 100 | 2529.1 |
|  | Form2T | 45 | 100 | 92.1 | 100 | 100 | 92.1 | 100 | 2501.6 |
|  | Form3T | 48 | 100 | 92.6 | 100 | 97.9 | 88.9 | 99.9 | 2300.2 |
|  | Meningitec ™ | 48 | 27.1 | 15.3 | 41.8 | 6.3 | 1.3 | 17.2 | 9.4 |
| SBA-MenY | Form 1T | 47 | 100 | 92.5 | 100 | 100 | 92.5 | 100 | 1987.4 |
|  | Form2T | 45 | 100 | 92.1 | 100 | 100 | 92.1 | 100 | 2464.8 |
|  | Form3T | 48 | 100 | 92.6 | 100 | 97.9 | 88.9 | 99.9 | 2033.7 |
|  | Meningitec ™ | 49 | 49.0 | 34.4 | 63.7 | 28.6 | 16.6 | 43.3 | 25.0 |

Vaccination with all three formulations of the ACWY-TT polysaccharide conjugate led to good SBA responses against MenA, MenC, MenW and MenY with 95-100% of subjects with titres greater than 1:8. In particular, the 5/5/5/5 and 2.5/10/2.5/2.5 formulations of the polysaccharide conjugates produced a higher response against MenC than the oligosaccharide Meningitec™ vaccine as seen by a higher proportion of subjects having a titre greater than 1:128 and the GMT readings.

TABLE 10

Seropositivity rates and GMCs for anti polysaccharide antibodies one month after vaccination

|  | Group | N | ≥0.3 µg/ml % | LL | UL | ≥2 µg/ml % | LL | UL | GMC µg/ml |
|---|---|---|---|---|---|---|---|---|---|
| Anti-MenA | Form 1T | 47 | 93.6 | 82.5 | 98.7 | 68.1 | 52.9 | 80.9 | 2.35 |
|  | Form2T | 45 | 100 | 92.1 | 100 | 64.4 | 48.8 | 78.1 | 3.11 |
|  | Form3T | 48 | 95.8 | 85.7 | 99.5 | 37.5 | 24.0 | 52.6 | 1.65 |
|  | Meningitec ™ | 50 | 10.0 | 3.3 | 21.8 | 2.0 | 0.1 | 10.6 | 0.18 |
| Anti-MenC | Form 1T | 47 | 100 | 92.5 | 100 | 100 | 92.5 | 100 | 9.57 |
|  | Form2T | 45 | 100 | 92.1 | 100 | 100 | 92.1 | 100 | 12.53 |
|  | Form3T | 47 | 100 | 92.5 | 100 | 97.9 | 88.7 | 99.9 | 19.29 |
|  | Meningitec ™ | 49 | 98.0 | 89.1 | 99.9 | 93.9 | 83.1 | 98.7 | 7.95 |
| Anti-MenW | Form 1T | 47 | 100 | 92.5 | 100 | 80.9 | 66.7 | 90.9 | 4.56 |
|  | Form2T | 45 | 100 | 92.1 | 100 | 93.3 | 81.7 | 98.6 | 6.83 |
|  | Form3T | 48 | 93.8 | 82.8 | 98.7 | 72.9 | 58.2 | 84.7 | 2.88 |
|  | Meningitec ™ | 50 | 0.0 | 0.0 | 7.1 | 0.0 | 0.0 | 7.1 | 0.15 |

TABLE 10-continued

Seropositivity rates and GMCs for anti polysaccharide antibodies one month after vaccination

| | Group | N | % | ≥0.3 µg/ml LL | UL | % | ≥2 µg/ml LL | UL | GMC µg/ml |
|---|---|---|---|---|---|---|---|---|---|
| Anti-MenY | Form 1T | 47 | 100 | 92.5 | 100 | 97.9 | 88.7 | 99.9 | 8.90 |
| | Form2T | 45 | 100 | 92.1 | 100 | 100 | 92.1 | 100 | 12.78 |
| | Form3T | 47 | 97.9 | 88.7 | 99.9 | 87.2 | 74.3 | 95.2 | 5.67 |
| | Meningitec ™ | 50 | 2.0 | 0.1 | 10.6 | 0.0 | 0.0 | 7.1 | 0.15 |

All three formulations of the ACWY-TT polysaccharide conjugate vaccine produced good immune responses against MenA, MenC, MenW and MenY with between 93% and 100% of subjects achieving titres grater than 0.3 µg/ml. Higher GMC readings were achieved using the 5/5/5/5 and 2/5/10/2.5/2.5 formulations of the ACWY-TT polysaccharide conjugate vaccine in comparison with Meningitec™.

Example 7—Comparison of Immunogenicity of Native and Sized MenY Polysaccharide Conjugates Mice (female DBA/2 of 6-8 wk) received two injections, 2 weeks apart, of PSY-TT by the subcutaneous route. Blood samples were taken 14 days after the second injection in order to perform anti-PSY ELISA and SBA using S1975 menY strain. Per injection, mice received 1 µg of PSY-TT (lyo non-ads formulation).

The conjugates described in table 11 were used.

TABLE 11

| Conjugates | ENYTT012 | ENYTT014 | ENYTT015 bis |
|---|---|---|---|
| PSY microfluidisation | NO | Yes (40 cycles) | Yes (20 cycles) |
| TT/PS ratio | 1/1 | 1/1 | 1/1 |

Results

The results (FIG. 1) show a trend towards higher immunogenicity for conjugates prepared using sized PSY. FIG. 1A shows the GMC results obtained in an ELISA for antisera raised against conjugates prepared from native MenY (ENYTT012), microfluidised MenY—40 cycles (ENYTT014) and microfluidised MenY—20 cycles (ENYTT015 bis). Higher GMCs were obtained where the MenY-TT was prepared from microfluidised MenY.

Similar results were obtained when the antisera were assessed by SBA assay (FIG. 1B). Again the higher GMT values were achieved using conjugates prepared from microfluidised MenY.

Example 8—Clinical Trial Assessing the Effect of a Linker in MenA in a MenACWY Conjugate Vaccine A single dose of different formulations of MenACWY vaccine was administered to teenagers of 15-19 years in 5 groups of 25 subjects in a 1:1:1:1:1 randomised trial. The formulations tested were:

F1—MenACWY conjugated to tetanus toxoid with the MenA conjugate containing an AH spacer—5/5/5/5 µg F2—MenACWY conjugated to tetanus toxoid with the MenA conjugate containing an AH spacer—2.5/5/2.5/2.5 µg F3—MenACWY conjugated to tetanus toxoid with the MenA conjugate containing an AH spacer—5/5/2.5/2.5 µg F4—MenACWY conjugated to tetanus toxoid with no spacer in any conjugate—5/5/5/5 µg Control group—Mencevax™ ACWY On day 30 after inoculation, a blood sample was taken from the patients.

The blood samples were used to assess the percentage of SBA-MenA, SBA-MenC, SBA-MenW135 and SBA-MenY responders one month after the vaccine dose. A vaccine response was defined as 1) for initially seronegative subjects—a post-vaccination antibody titre ⅟32 at 1 month or 2) for initially seropositive subjects—antibody titre of 4 fold the pre-vaccination antibody titre.

Results

As shown in Table 12, the use of a spacer in the MenA conjugate led to an increased immune response against MenA. The percentage of responders rose from 66% to 90-95% when the AH spacer was added. This was reflected in an increase in SBA GMT from 4335 to 10000 and an increase in GMC from 5 to 20-40. Surprisingly, the use of an AH spacer also led to an increased immune response against MenC as seen by an increase in the percentage of responders and an increase in the SBA GMT. An increase could also be seen in the SBA-GMT against MenY (6742-7122) and against MenW (4621-5418) when a spacer was introduced.

TABLE 12

| Formulation | % SBA MenA responders | SBA-MenA GMT | Anti-PSA GMC µg/ml ELISA |
|---|---|---|---|
| F 1 5AH/5/5/5 | 90.9 | 9805 | 20.38 |
| F2 2.5AH/5/2.5/2.5 | 75 | 8517 | 29.5 |
| F3 5AH/5/2.5/2.5 | 95.5 | 10290 | 47.83 |
| F4 5/5/5/5 | 66.7 | 4335 | 5.46 |
| Mencevax ™ | 85.7 | 8022 | 27.39V |

| Formulation | % SBA MenC responders | SBA-MenC GMT | Anti-PSC GMC µg/ml ELISA |
|---|---|---|---|
| F 1 5AH/5/5/5 | 69.6 | 3989 | 12.11 |
| F2 2.5AH/5/2.5/2.5 | 81.8 | 3524 | 12.78 |
| F3 5AH/5/2.5/2.5 | 81.8 | 3608 | 8.4 |
| F4 5/5/5/5 | 73.9 | 2391 | 8.84 |
| Mencevax ™ | 90.0 | 5447 | 38.71 |

| Formulation | % SBA MenW responders | SBA-MenW GMT | Anti-PSW GMC µg/ml ELISA |
|---|---|---|---|
| F 1 5AH/5/5/5 | 95 | 5418 | 9.65 |
| F2 2.5AH/5/2.5/2.5 | 85 | 4469 | 14.55 |
| F3 5AH/5/2.5/2.5 | 95.5 | 4257 | 6.39 |
| F4 5/5/5/5 | 95.5 | 4621 | 10.7 |
| Mencevax ™ | 86.4 | 2714 | 13.57 |

| Formulation | % SBY MenY responders | SBA-MenY GMT | Anti-PSY GMC µg/ml ELISA |
|---|---|---|---|
| F 1 5AH/5/5/5 | 91.3 | 7122 | 16.3 |
| F2 2.5AH/5/2.5/2.5 | 87.5 | 5755 | 12.52 |
| F3 5AH/5/2.5/2.5 | 80 | 5928 | 8.88 |
| F4 5/5/5/5 | 91.3 | 6742 | 13.88 |
| Mencevax ™ | 91.7 | 4854 | 21.02 |

Example 9—Clinical Trial Assessing the Effect of a Linker in MenA and MenC Conjugates in a MenACWY Conjugate Vaccine A single dose of different formulations of MenACWY vaccine was administered to teenagers of 15-19 years in 5 groups of 25 subjects in a 1:1:1:1:1 randomised trial. The formulations tested were:

F1—MenACWY conjugated to tetanus toxoid with the MenA and MenC conjugates containing an AH spacer—2.5/2.5/2.5/2.5 µg F2—MenACWY conjugated to tetanus toxoid with the MenA and MenC conjugates containing an AH spacer—5/5/2.5/2.5 µg F3—MenACWY conjugated to tetanus toxoid with the MenA and MenC conjugates containing an AH spacer—5/5/5/5 µg F4—MenACWY conjugated to tetansus toxoid with the MenA conjugate containing an AH spacer—5/5/5/5 µg Control group—Mencevax™ ACWY On day 30 after inoculation, a blood sample was taken from the patients.

The blood samples were used to assess the percentage of SBA-MenA, SBA-MenC, SBA-MenW135 and SBA-MenY responders one month after the vaccine dose. A vaccine response was defined as 1) for initially seronegative subjects—a post-vaccination antibody titre ≥1/32 at 1 month or 2) for initially seropositive subjects—antibody titre of ≥4 fold the pre-vaccination antibody titre.

Results

The introduction of an AH spacer into the MenC conjugate led to an increase in the immune response against MenC as shown in Table 13. This is demonstrated by an increase in SBA GMT from 1943 to 4329 and an increase in anti-PSC GMC from 7.65 to 13.13. Good immune responses against MenA, MenW and MenY were maintained.

TABLE 13

| Formulation | % SBA MenA responders | SBA-MenA GMT | Anti-PSA GMC µg/ml ELISA |
|---|---|---|---|
| F 12.5AH/2.5AH/2.5/2.5 | 75 | 8417 | 20.23 |
| F2 5AH/5AH/2.5/2.5 | 72 | 6299 | 16.07 |
| F3 5AH/5AH/5/5 | 87 | 9264 | 27.26 |
| F4 5AH/5/5/5 | 77.3 | 9632 | 20.39 |
| Mencevax ™ | 78.3 | 8284 | 12.93 |

| Formulation | % SBA MenC responders | SBA-MenC GMT | Anti-PSC GMC µg/ml ELISA |
|---|---|---|---|
| F 12.5AH/2.5AH/2.5/2.5 | 88 | 3619 | 12.82 |
| F2 5AH/5AH/2.5/2.5 | 88 | 2833 | 13.32 |
| F3 5AH/5AH/5/5 | 95.8 | 4329 | 13.13 |
| F4 5AH/5/5/5 | 95.8 | 1943 | 7.65 |
| Mencevax ™ | 91.7 | 1567 | 16.55 |

| Formulation | % SBA MenW responders | SBA-MenW GMT | Anti-PSW GMC µg/ml ELISA |
|---|---|---|---|
| F 12.5AH/2.5AH/2.5/2.5 | 100 | 5656 | 7 |
| F2 5AH/5AH/2.5/2.5 | 96 | 4679 | 5.4 |
| F3 5AH/5AH/5/5 | 91.3 | 4422 | 4.45 |
| F4 5AH/5/5/5 | 88 | 4947 | 7.67 |
| Mencevax ™ | 96 | 3486 | 11.93 |

TABLE 13-continued

| Formulation | % SBY MenY responders | SBA-MenY GMT | Anti-PSY GMC µg/ml ELISA |
|---|---|---|---|
| F 1 2.5AH/2.5AH/2.5/2.5 | 75 | 3891 | 17.81 |
| F2 5AH/5AH/2.5/2.5 | 92 | 3968 | 11.96 |
| F3 5AH/5AH/5/5 | 79.2 | 2756 | 9.51 |
| F4 5AH/5/5/5 | 80 | 3914 | 16.76 |
| Mencevax ™ | 88 | 3056 | 21.41 |

The invention claimed is:

1. An immunogenic composition, comprising:
    (a) a *Neisseria meningitidis* (*N. meningitides*) serogroup A capsular saccharide conjugated to an adipic acid dihydrazide (ADH) linker, wherein the linker is conjugated to tetanus toxoid carrier protein;
    (b) a *N. meningitidis* serogroup C capsular saccharide conjugated to an adipic acid dihydrazide (ADH) linker, wherein the linker is conjugated to tetanus toxoid carrier protein;
    (c) a *N. meningitidis* serogroup W capsular saccharide directly conjugated to tetanus toxoid carrier protein in the absence of a linker; and
    (d) a *N. meningitidis* serogroup Y capsular saccharide directly conjugated to tetanus toxoid carrier protein in the absence of a linker;
    wherein the ratio of Men A saccharide to carrier protein is between 1:2 to 1:5 (w/w); and wherein the ratio of MenC saccharide to carrier protein is between 1:2 to 1:5 (w/w).

2. The immunogenic composition of claim 1, wherein the ratio of Men W and/or Y saccharide to carrier protein is between 1:0.5 and 1:2 (w/w).

3. The immunogenic composition of claim 1, wherein the composition does not include an adjuvant.

4. The immunogenic composition of claim 1, wherein the composition does not include an aluminum salt adjuvant.

5. The immunogenic composition of claim 1, further comprising sucrose.

6. The immunogenic composition of claim 1, further comprising a *N. meningitidis* serogroup B outer membrane vesicle preparation or capsular saccharide.

7. The immunogenic composition of claim 1, further comprising *Haemophilus* influenza (*H. influenzae*) b capsular saccharide conjugated to a carrier protein, the carrier protein selected from the group consisting of tetanus toxoid, diphtheria toxoid, cross reactive material 197, fragment C of tetanus toxoid and protein D, wherein the *H. influenzae* b conjugate is present in a lower dose than the dose of any other bacterial saccharide conjugate.

8. The immunogenic composition of claim 1, wherein the *H. influenzae* b capsular saccharide (Hib) is conjugated to tetanus toxoid.

9. A pharmaceutical composition, comprising the immunogenic composition of claim 1 and a pharmaceutically acceptable excipient.

10. A process for making a vaccine, comprising the step of mixing the immunogenic composition of claim 1 with a pharmaceutically acceptable excipient.

11. A method of immunizing a human host against disease caused by *Neisseria meningitidis* infection, comprising administering to the host an immunoprotective dose of the immunogenic composition of claim 1.

* * * * *

UNITED STATES PATENT AND TRADEMARK OFFICE
CERTIFICATE OF CORRECTION

PATENT NO. : 10,245,317 B2
APPLICATION NO. : 15/265597
DATED : April 2, 2019
INVENTOR(S) : Ralph Leon Biemans et al.

Page 1 of 1

It is certified that error appears in the above-identified patent and that said Letters Patent is hereby corrected as shown below:

In the Claims

Column 40, Claim 8, Line 51:
"composition of claim 1," should read -- composition of claim 7, --.

Signed and Sealed this
Seventeenth Day of March, 2020

Andrei Iancu
*Director of the United States Patent and Trademark Office*